(12) United States Patent
Jersey-Willuhn et al.

(10) Patent No.: US 7,169,107 B2
(45) Date of Patent: Jan. 30, 2007

(54) CONDUCTIVITY RECONSTRUCTION BASED ON INVERSE FINITE ELEMENT MEASUREMENTS IN A TISSUE MONITORING SYSTEM

(76) Inventors: Karen Jersey-Willuhn, 702 Val Sereno Dr., Olivenhain, CA (US) 92024; Manuchehr Soleimani, Burlington Street, Manchester (GB) M15 6HR ( * ) Notice: Subject to any disclaimer, the term of this patent is extended or adjusted under 35 U.S.C. 154(b) by 868 days.

(21) Appl. No.: 10/227,175

(22) Filed: Aug. 23, 2002

(65) Prior Publication Data

US 2003/0216630 A1    Nov. 20, 2003

Related U.S. Application Data

(60) Provisional application No. 60/351,094, filed on Jan. 25, 2002.

(51) Int. Cl.
*A61B 8/00* (2006.01)

(52) U.S. Cl. .................. 600/442; 600/407; 600/547

(58) Field of Classification Search ................ 600/442, 600/547
See application file for complete search history.

(56) References Cited

U.S. PATENT DOCUMENTS

| | | | |
|---|---|---|---|
| 4,328,409 A | 5/1982 | Senn |
| 4,416,288 A | 11/1983 | Freeman |
| 4,448,204 A | 5/1984 | Lichtenstein |
| 4,486,835 A | 12/1984 | Bai et al. |
| 4,493,039 A | 1/1985 | Gregory |
| 4,540,002 A | 9/1985 | Atlas |
| 4,647,281 A | 3/1987 | Carr |
| 4,877,034 A | 10/1989 | Atkins et al. |
| 5,120,813 A | 6/1992 | Ward, Jr. |
| 5,198,776 A | 3/1993 | Carr |
| 5,334,141 A | 8/1994 | Carr et al. |
| 5,337,748 A | 8/1994 | McAdams et al. |
| 5,353,802 A | 10/1994 | Ollmar |
| 5,428,123 A | 6/1995 | Ward et al. |
| 5,765,563 A | 6/1998 | Vander Schaaf |
| 5,800,350 A * | 9/1998 | Coppleson et al. ......... 600/372 |
| 5,897,519 A | 4/1999 | Shesol et al. |
| 5,947,910 A | 9/1999 | Zimmet |
| 5,954,668 A | 9/1999 | Uber, III et al. |
| 5,964,703 A | 10/1999 | Goodman et al. |
| 6,055,448 A | 4/2000 | Anderson et al. |

(Continued)

OTHER PUBLICATIONS

Mohd Zaid Abdullah, 1999, Int. J Elect. Enging. Educ., vol. 36, pp. 311-324.*

(Continued)

*Primary Examiner*—Brian L. Casler
*Assistant Examiner*—Ashish Jasani
(74) *Attorney, Agent, or Firm*—Koestner Bertani LLP; Ken J. Koestner

(57) ABSTRACT

An impedance model of tissue is useful for describing conductivity reconstruction in tissue. Techniques for determining and mapping conductivity distribution in tissue supply useful information of anatomical and physiological status in various medical applications. Electrical Impedance Tomography (EIT) techniques are highly suitable for analyzing conductivity distribution. Electrical characteristics of tissue include resistive elements and capacitive elements. EIT techniques involve passing a low frequency current through the body to monitor various anatomical and physiological characteristics. The system can interrogate at multiple frequencies to map impedance. Analytical techniques involve forward and inverse solutions to boundary value analysis to tissue characteristics.

19 Claims, 17 Drawing Sheets

U.S. PATENT DOCUMENTS

| | | |
|---|---|---|
| 6,270,455 B1 | 8/2001 | Brown |
| 6,289,238 B1 | 9/2001 | Besson et al. |
| 6,290,681 B1 | 9/2001 | Brown |
| 6,360,123 B1 | 3/2002 | Kimchi et al. |
| 6,408,204 B1 | 6/2002 | Hirschman |
| 6,425,878 B1 | 7/2002 | Shekalim |

OTHER PUBLICATIONS

Yorkey, Thomas J., Ph.D., 1986, The University of Wisconsin—Madison, 180 pages; AAT 8621942.*

Robert S. Ward; Kathleen A. White, Barrier Films that Breathe, Chemtech, Nov. 1991; pp. 670-676.

A. Lozano, J. Rosell, P.J. Riu and R. Pallas-Areny, Segmental Body Fluid Shift Estimation During HDT Positions by Electrical Impedance Measurements, Proceedings of the IX International Conference on Electrical Bio-Impedance, Sep. 26-30, 1995, pp. 233-236, Heidelberg, Germany.

E.J. Woo; P. Hua; J.G. Webster; W.J. Tompkins; R. Pallas-Areny, Skin Impedance Measurements Using Simple and Compound Electrodes.. Medical and Biological Engineering and Computing. 30(1): 97-102, Jan. 1992.

Carolyn B. Yucha; Marie Hastings-Tolsma; Nikolaus M. Szeverenyi; Joy M. Tompkins; and Linda Robson, Characterization of Intravenous Infiltrates. Applied Nursing Research (Research Briefs, Edited by Patricia H. Byers), vol. 4, No. 4 Nov. 1991; pp. 184-186.

Carolyn B. Yucha, RN, PHD, Marie Hastings-Tolsma, RNC, PHD, and Nikolaus M. Szeverenyi, PHD, Differences Among Intravenous Extravasations Using Four Common Solutions. Journal of Intravenous Nursing, vol. 16, No. 5, Sep./Oct. 1993; pp. 277-281.

Robert S. Ward, Tailored polyurethanes with Functional Blocks for Biomedical Applications. Contemporary Biomaterials Through Precise Control of Macromolecular Chemistry and Architecture, American Chemical Society Symposium, Nov. 19-22, Williamsburg, Virginia; pp. 1-3.

Jill E. Jacobs, MD, Bernard A. Birnbaum, MD, Curtis P. Langlotz, MD, PHD, Contrast Media Reactions and Extravasation: Relationship to Intravenous Injection Rates. Radiology. 209:411-416, Nov. 1998.

Albert Lozano-Nieto, PHD., Human Body Composition Determination; Anaylysis of Methods and Techniques. Journal of Clinical Engineering. Nov./Dec. 1998; pp. 416-422

Bernard A. Birnbaum, MD; Rendon C. Nelson, MD; Judith L. Chezmar, MD; and Seth N. Glick, MD. Extravasation Detection Accessory: Clinical Evaluation in 500 Patents. Radiology. 212:421-438, Aug. 1999.

Albert Lozano-Nieto, PH.D. Clinical Applications of Bioelectrical Impedance Measurements. Journal of Clinical Engineering. Jul./Aug. 2000; pp. 211-218.

* cited by examiner

CONDUCTIVITY RECONSTRUCTION BASED ON INVERSE FINITE ELEMENT MEASUREMENTS IN A TISSUE MONITORING SYSTEM

RELATED PATENTS AND APPLICATIONS

This application is related to U.S. patent application Ser. No. 60/351,094, filed on Jan. 25, 2002.

The disclosed system and operating method are related to subject matter disclosed in the following co-pending patent applications that are incorporated by reference herein in their entirety:

1. U.S. patent application Ser. No. 10/227,150 entitled, "Tissue Monitoring System for Intravascular Infusion", <attorney docket no.: 1013.P001 US> naming Karen Jersey-Willuhn and Manuchehr Soleimani as inventors and filed on even date herewith;

2. U.S. patent application Ser. No. 10/227,648 entitled, "Film Barrier Dressing for Intravascular Infusion Tissue Monitoring System", <attorney docket no.: 1013.P002 US> naming Karen Jersey-Willuhn and Manuchehr Soleimani as inventors and filed on even date herewith.

BACKGROUND OF THE INVENTION

1. Field of the Invention

The invention relates generally to physiological monitoring devices and, more particularly, to tissue monitoring devices and methods for detecting harmful conditions including conditions that occur during intravascular infusion.

2. Relevant Background

An infusion system is commonly used to infuse a fluid into a patient's vascular system. Intravenous (IV) therapy is sometimes necessary for patient treatment and is generally considered a safe procedure. IV therapy is administered to approximately 80% of hospitalized patients in the United States. Some form of IV complication develops in nearly a third of patients receiving IV therapy. Most complications do not progress to more serious problems, but cases with further complications of IV failure are difficult to predict.

Several complications may arise from the infusion process including extravasation, tissue necrosis, infiltration, phlebitis, venous inflammation, and others. These complications can result in prolonged hospitalization, infections, patient discomfort, patient disfigurement, nerve damage, and additional medical complications and expense. Phlebitis is the largest cause of intravascular infusion morbidity. Infiltration and extravasation follow only phlebitis as IV morbidity causes.

When complications of infiltration, extravasation, phlebitis, or blood clots occur, the standard of care requires prompt removal of the IV to minimize further complications since continued pumping of infusate exacerbates the complications. Immediate detection of complications and termination of infusion reduces the possibility and damage of further complications. IV complications can cause failure to infuse a needed drug or fluid and lead to inadequate or sub-optimal therapeutic drug levels and hypo-volemia. Fluids that would lead to patient recovery may fail to reach the appropriate organs or tissue. Under life-threatening conditions or where infusion is life-sustaining, a patient's failure to receive fluids can be lethal. IV failure compromises patient safety.

Infiltration is the inadvertent administration of solution into surrounding tissue. Extravasation is the inadvertent administration of a solution that is capable of causing tissue necrosis when the material escapes or is infused outside the desired vascular pathway.

Extravasation sometimes results when an injection fluid, for example a contrast medium, is injected into a blood vessel. Extravasation is the accidental infusion of injection fluid into tissue surrounding a blood vessel rather than into the intended blood vessel. Various causes of complications that may occur with intravenous infusions include fragile vasculature, valve disease, inappropriate needle placement, infusion needle dislodgement of the cannula or needle delivering the fluid, microdilation of veins due to infusate chemical properties causing the material to leak from the vein dislodgement from the vessel due to patient movement, or infusion needle piercing through the vessel wall also due to patient movement. IV complication risk increases for elderly persons, children, cancer patients, and immunocompromised patients.

Patients under therapy with vesicant drugs including chemotherapy, infusion of highly osmotic solutions, or high acid or low base solutions have risk of tissue necrosis if fluids are infused outside the vascular pathway. Examples infused agents include total parenteral nutrients, chemotherapeutic alkalating drugs, alkaline solutions, vasopressors (for example, Total Parenteral Nutrition (TPN)), antibiotics, hypertonic acids, KCl, and others. Many routinely-used antibiotics and medications are capable of causing extravasations and tissue necrosis. Antineoplastics can cause severe and widespread tissue necrosis if extravasation occurs. Chemotherapeutic agents are highly toxic IV drugs. Several drugs for emergency use have a well-documented high incidence of tissue damage. For example, administration of essential vasopressor drug dopamine in life-threatening or life-sustaining situations has a documented incidence of 68% tissue necrosis or extravasation at the IV infusion site. Caretakers cannot anticipate which complication will progress including necrosis to muscle.

Complications that may occur can cause serious patient injury by tissue trauma and toxicity of injection fluid. For example some injection fluids such as contrast media or chemotherapy drugs can be toxic to tissue if undiluted by blood flow. As a consequence, extravasation should be detected as early as possible and injection immediately discontinued upon detection.

In infiltration and extravasation, a condition occurs in which infused fluid enters extravascular tissue rather than the blood stream occurring, for example, when an infusion needle is not fully inserted to the interior of a blood vessel. Infiltrating fluid is infused into interstitial spaces between tissue layers, preventing proper intravenous drug administration and possibly resulting in toxic or caustic effects of direct contact of infused fluids with body tissues.

Infiltration and extravasation complications are costly and compromise patient outcome. Complications include pain and prolonged discomfort that may last for months, prolonged healing, ischemic necrosis due to vasoconstriction, opportunistic infections and septicemia, ulceration, cosmetic and physical disfigurement, and direct cellular toxicity for antineoplastic agents. Other complications include skin grafting, flaps, and surgical debridements, sometimes multiple. Further complications are compartment syndrome, arteriolar compression, vascular spasm, nerve damage (sometimes permanent), muscular necrosis, functional muscular changes, functional loss of extremities, amputation, reflex sympathetic dystrophy, and chronic pain syndrome.

Infiltration and extravasation can cause catheter-related bloodstream infection, including sepsis. An estimated 200, 000 to 400,000 incidences of catheter-related infections occur annually, resulting in approximately 62,500 deaths, 3.5 million additional hospital days for treatment, and adds about $3.5 billion to the annual healthcare cost. Estimates of individual costs vary. A catheter-related bloodstream infection may cost $6,000 to $10,000 per incidence, and increase the hospital stay by up to 22 days.

Additional costs can be incurred. Additional medications may need to be injected to dilute or neutralize the effect of toxic drugs once tissue necrosis has begun to decrease the caustic reaction and reduce tissue damage. Surgical removal of the necrotic tissue may be required. Caretaker time, and therefore costs, increase since the extremities typically need to be elevated to improve venous return, warm and cool packs are applied, psychological comfort and pain medications given, and severity of the complication is monitored. A septic infection may cause a serious infection such as an infection in the heart.

Other conditions that result from improper supply of fluid to a patient in intravenous therapy include venous inflammation and phlebitis, swelling at the infusion site. Phlebitis complications include inflammation or thrombophlebitis that occurs with about 10% of all infusions. If phlebitis continues as the duration of infusion continues, the duration of the complication also increases. Phlebitis predisposes a patient to local and systemic infection. Phlebitis often results in a complication of infection resulting from use of intravenous lines. Underlying phlebitis increases the risk of infection by an estimated twenty times with estimated costs of IV infections between $4000 and $6000 per occurrence. When phlebitis is allowed to continue, the vein becomes hard, tortuous, tender, and painful for the patient. The painful condition can persist indefinitely, incapacitates the patient, and may destroy the vein for future use. Early assessment of complication and quick response can reduce or eliminate damage and save the vein for future use.

Another possible complication is blood clotting. IV needles and cannulas can become occluded with blood clots. As an occlusion intensifies, mechanical failure of the infusion can occur. Prescribed therapy cannot be administered if the catheter is occluded and multiple other complications can result, such as pulmonary embolism. Complications may progress, forming a thrombus and causing thrombophlebitis, or catheter-associated infections or bactermias.

Tissue necrosis may result when some of the infused materials are vesicant or other materials are infused outside the vascular pathway.

The current methods for detecting phlebitis, necrosis, infiltration or extravasation in a medical surgical patient undergoing therapeutic infusion are visual inspection and notification of pain by the patient. A caretaker visually inspects the intravascular insertion site or affected body parts for swelling, tenderness, discoloration. Otherwise, the caretaker requests or receives notification of pain by the patient but generally when tissue damage has begun.

Another problem that occurs with infusion is that the patient normally does not eat so that vital electrolytes can be lacking, a condition that is exacerbated by the patient's illness. One critical electrolyte is potassium. Medical protocols exist to replace needed potassium, but the level of replacement is difficult to determine. Low or high levels of potassium can lead to cardiac irritability and other complications. Electrolyte levels are commonly determined by electrochemistry testing, usually by blood draws, a painful procedure that commonly involves time delays for analysis.

What are needed are safe, reliable devices and methods that supply information on patient status of the presence or absence of IV complications. What are further needed are devices and methods that notify a caretaker of the occurrence of infiltration, extravasation, phlebitis, blood clots, and electrolyte levels with sufficient quickness to reduce or eliminate tissue damage, patient discomfort, and additional complications and associated costs.

SUMMARY OF THE INVENTION

A device is capable of executing non-invasive physiological measurements to characterize physiologic information from cross-sectional surface and subcutaneous tissue in one, two, or three dimensions to detect the presence or absence of tissue conditions such as infiltration or extravasation during intravascular infusion. In some embodiments, the device utilizes depth-selective methods to sense, detect, quantify, monitor, and generate an alert notification of tissue parameters.

An impedance model of tissue is useful for describing conductivity reconstruction in tissue. Techniques for determining and mapping conductivity distribution in tissue supply useful information of anatomical and physiological status in various medical applications. Electrical Impedance Tomography (EIT) techniques are highly suitable for analyzing conductivity distribution. Electrical characteristics of tissue include resistive elements and capacitive elements. EIT techniques involve passing a low frequency current through the body to monitor various anatomical and physiological characteristics. The system can interrogate at multiple frequencies to map impedance. Analytical techniques involve forward and inverse solutions to boundary value analysis to tissue characteristics.

An Electrical Impedance Tomography technique uses a regularized Newton-Raphson method to optimize the ill-posed inverse problem for imaging and mapping. The optimization problem attempts to find a best conductivity distribution that fits measured data. Image reconstruction uses nr to optimize the ill-posed inverse problem for imaging and mapping. The optimization problem attempts to find a best conductivity distribution that fits measured data. Image reconstruction uses Newton-Raphson regularization to stabilize the numerical solution of the ill-posed inverse problem. Image reconstruction based on the Newton-Raphson method uses an efficient method for Jacobian matrix computation. Tikhonov regularization is used in the Newton-Raphson method to stabilize image reconstruction.

The inverse problem in three-dimensional Electrical Impedance Tomography imaging is ill-posed and nonlinear. Several methods can be used for image reconstruction of both low and high contrast conductivity. EIT imaging can be cased on the Born approximation, particularly for low contrast conductivity reconstruction where little advantage is gained in recalculation of the Jacobian.

In a system that does not include a barrier film, the sensor frame film can be used to map a tumor for excision. During minimally invasive surgeries such as radiofrequency ablation, lasers and cryotherapy as well as endoscopes, a surgeon uses an ultrasound to visualize the lesions. Visualization of the tissue is difficult. A system that allows a surgeon to assess when adequate tissue for the lesion has been removed and prevents removal of healthy tissue is desired. Using the illustrative frame around a site enables a surgeon to map the end of the lesion for discriminating good tissue and cancerous tissue. The capability is especially useful with a thermograhic map for cryotherapy.

Various aspects of the illustrative infiltration detection system may be utilized individually or in combination and are useful to identify an abnormal infusion as early as possible without generating an excessive number of false alarms. Aspects include an at least partially transparent film barrier dressing, sensors combined into the dressing, parameter modeling using one or more sensing technologies, condition detection using pattern recognition, generation of an alarm signal or annunication, generation of signals to control operation of an infusion pump, and others. Early detection allows attending medical staff to rectify problems before significant damage occurs due to infiltration and before the patient has been deprived of a significant amount of the intravenous therapy.

BRIEF DESCRIPTION OF THE DRAWINGS

The features of the described embodiments believed to be novel are specifically set forth in the appended claims. However, embodiments of the invention relating to both structure and method of operation, may best be understood by referring to the following description and accompanying drawings.

DESCRIPTION OF THE EMBODIMENT(S)

Figure 1:
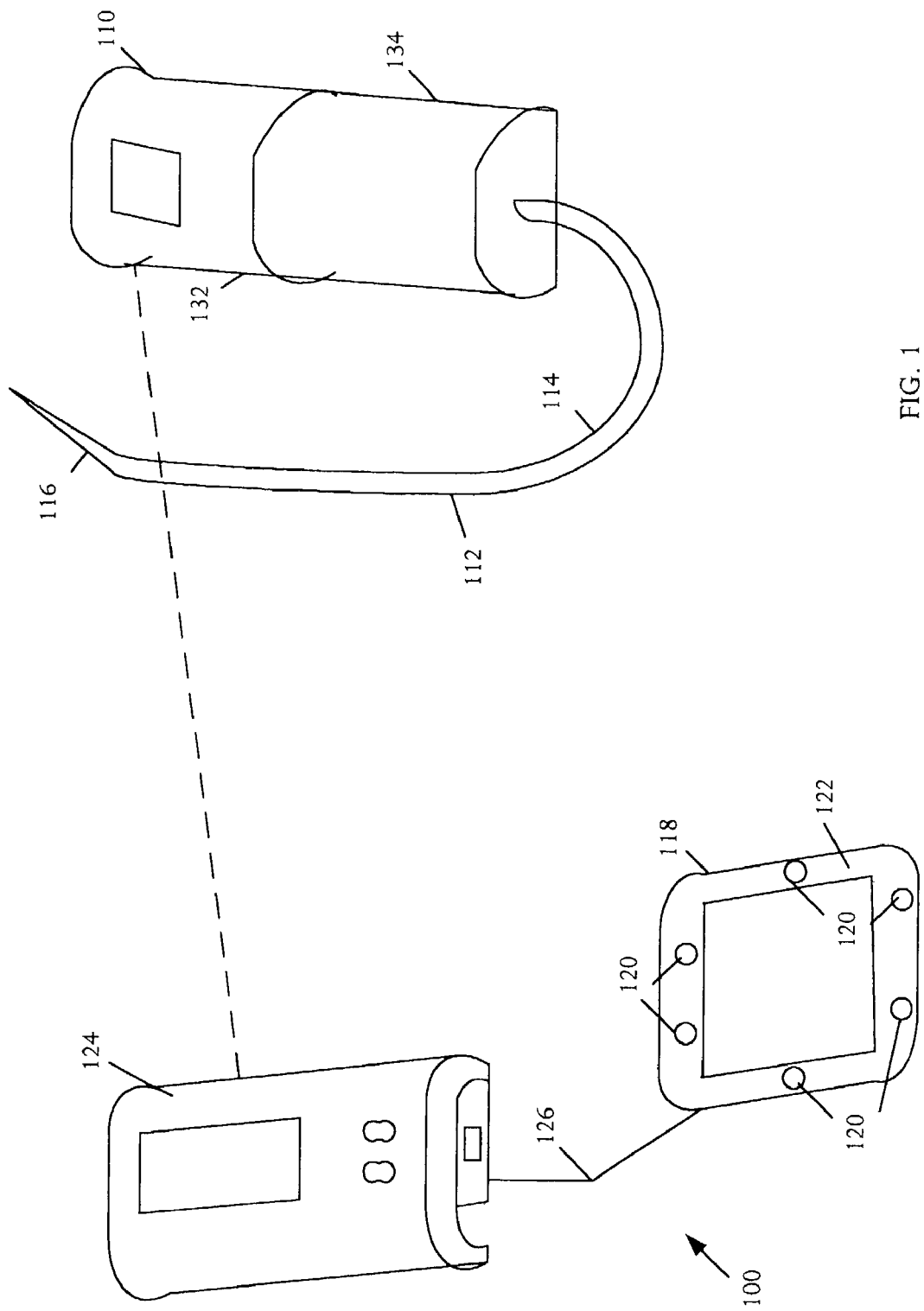
FIG. 1 is a schematic pictorial diagram that illustrates an infusion system with a capability to monitor tissue conditions.

Referring to FIG. 1, a schematic pictorial diagram illustrates an infusion system 100 with a capability to monitor tissue conditions. The infusion system 100 can be used to infuse a flowable material or fluid in the form of liquid, gas, or a combination into a patient. The illustrative infusion system 100 includes an infusion device 110 that delivers the infusion fluid and a conduit 112 for conducting the flowing material from the infusion device 110 to the patient. The conduit 112 comprises a flexible tubing 114 that couples to the infusion device 110 and a cannula 116, such as a needle or catheter, that is capable of inserting into the patient's vascular system.

The infusion system 100 is a noninvasive system that can be applied to the surface skin for monitoring in one or more dimensions using depth-selective cross sectional surface and subcutaneous tissue over time in a patient receiving an intravascular infusion to measure and characterize tissue conditions. The infusion system 100 can be used to detect and notify an individual of the presence or absence of physiological conditions that may indicate tissue complications such as tissue infiltration and extravasation during intravascular infusions.

The infusion system 100 also comprises a sensor dressing 118 with sensors 120 integrated into a film barrier dressing 122, a sensor signal pathway 126, and a control unit 124 that controls monitoring, analysis, and notification of tissue condition. The sensor signal pathway 126 can connect between the film barrier dressing 122 and the control unit 124, carrying data and control signals. The sensor signal pathway 126 can be of any suitable technology including conductive wires, fiberoptic channels, wireless channels, and others.

The film barrier dressing 122 is a tissue-contacting section that is capable of temporary affixation to surface tissue over one or more tissue sites, typically including an intravascular insertion site. The film barrier dressing 122 protects the skin and tissue in the vicinity of the infusion against exposure to pathogens in the environment, reducing the possibility of infection, and secures the catheter to reduce or eliminate motion that may result in complications. The film barrier dressing 122 is transparent or includes a transparent or clear window to allow visual of the infusion site and forms a structural support for the sensors 120. The film barrier dressing 122 has one or more adhesive layers capable of contacting and affixing to patient tissue and also capable of securing a needle or intravenous catheter against the skin and sealing the top of an intravascular insertion.

In some embodiments, the film barrier dressing 122 is a tissue contacting dressing that at least partially attaches to tissue and contains a polymer adhesive suspended in a neutral protein compound. The adhesive can be loosened or removed by applying water or alcohol.

The sensors 120 can be of a single type or multiple types and are capable of detecting signals using one or more sensing technologies. Suitable sensor types include bio-impedance, spectrometry, spectrophotometer, oximeter, photonics, other optical technology, magnetoresistive, micro-electro-mechanical system (MEMS) sensors, acoustic sensors, and others.

In some examples, the sensors 120 contain one or more elements capable of sending and receiving signals from tissue in one or more body locations. The sensors 120 comprise one or more sensor arrays adapted for transmitting signals into tissue and receiving signals from the tissue using one or more sensing technologies.

In one particular example, the sensors 120 acquire signals using two sensor technologies including a bio-impedance sensor and an optical sensor. Other embodiments may include only a single sensor, other types of sensors, or more than two sensors. The bio-impedance sensor is connected to the control unit 124 via an electrically-conductive sensor pathway and a spectrophotometry sensor is connected to the control unit 124 using a fiberoptic light pipeline. The control unit 124 analyzes the bio-impedance information in combination with the spectrophotometric information are compared to threshold and/or historical stored values to monitor tissue for detection and notification of tissue conditions such as extravasation and infiltration.

In some embodiments, an infusion system 100 utilizes a plurality of sensing technologies to improve reliability and reduce or eliminate the occurrences of false alarms. The control unit 124 can utilize information obtained using the multiple sensing technologies, store and analyze a time history of the information using various techniques such as thresholding and pattern recognition.

The infusion system 100 can be used to deliver fluid for various purposes including patient hydration, nutrient delivery, therapeutic drug delivery, diagnostic testing, supply of blood components or other healthcare materials. During operation, the infusion device 110 delivers infusion fluid through the flexible tubing 114 and the cannula 116 into the patient's vascular system.

The infusion system 100 is suitable for use in any suitable IV setting, such as routine patient care in medical surgical units, operating room ambulatory care centers, home healthcare for patients undergoing intravenous therapeutic treatment, and others.

The control unit 124 obtains and stores information from the sensors 120. Depending on the particular sensing technology, the control unit 124 may include various signal conditioners and processors to configure the information more suitably for subsequent analysis and storage.

For some sensor technologies such as sensors that acquire electrical information in one or more frequency bands, the control unit 124 includes a multiple gain amplifier circuit. In one example, the amplifier circuit may have multiple filter stages (not shown) such as a high-gain stage, a medium-gain stage, and a low-gain stage connected in a cascade configuration. The cascaded filter is coupled to an analog to digital converter (not shown) that can convert the sensed information for analysis and storage under control of a processor (not shown).

The processor may be any suitable type such as a microprocessor, a controller a microcontroller, a central processing unit (CPU), a digital signal processor (DSP), a state machine, discrete logic, or the like. The processor can be programmed to perform a variety of analysis, storage, and control functions. In one example, the processor includes a program for generating data images from processed signals that are indicative of tissue condition. The processor also includes a control program for controlling signals acquisition by the sensors 120. The processor may include a communication program for communicating information to a remote location, enabling remote surveillance of tissue measurements and characteristics.

The infusion system 100 detects and monitors one or more conditions including blood clots, phlebitis, tissue necrosis, and intravascular infiltration and extravasation associated with the infusion of a flowable material in a vascular pathway. The infusion system 100, upon detection of one or more particular conditions, can generate a detection signal, a status and alarm notification, giving medical surveillance of the status of tissue as a patient receives an infusion. The surveillance signal notifies a health care provider or caretaker to intervene early to avoid intravascular complications. The alarm may be an audible sound, a warning screen display for a computer, a vibration or buzzer annunciation, flashing lights, or any other suitable signal. The notification signal may be delivered to a proximal or remote location.

The control unit 124 may have an alarm or enunciator that enables a caretaker, for example a nurse, positioned in a remote location to supervise a patient's infusion. The infusion system 100 can be configured as a safe, efficient, inexpensive, and reliable monitoring device for early detection of infiltration, extravasation, and other complications that is suitable for use both inside and out of a hospital environment. The sensor dressing 118 can be applied at the perivascular area at the site of the intravascular insertion and also at body locations remote from the insertion that are at risk of fluid collection due to infiltration and extravasation.

In some embodiments, the control unit 124 is capable of communicating with an infusion controller 132 that is a component of the infusion device 110 to control an infusion pump 134. The infusion system 100 monitors patient tissue condition and, under control of a surveillance program executing in the control unit 124, can detect harmful tissue conditions and reduce complications by adjusting infusion flow or terminate infusion in response to the alarm condition.

Figure 2:
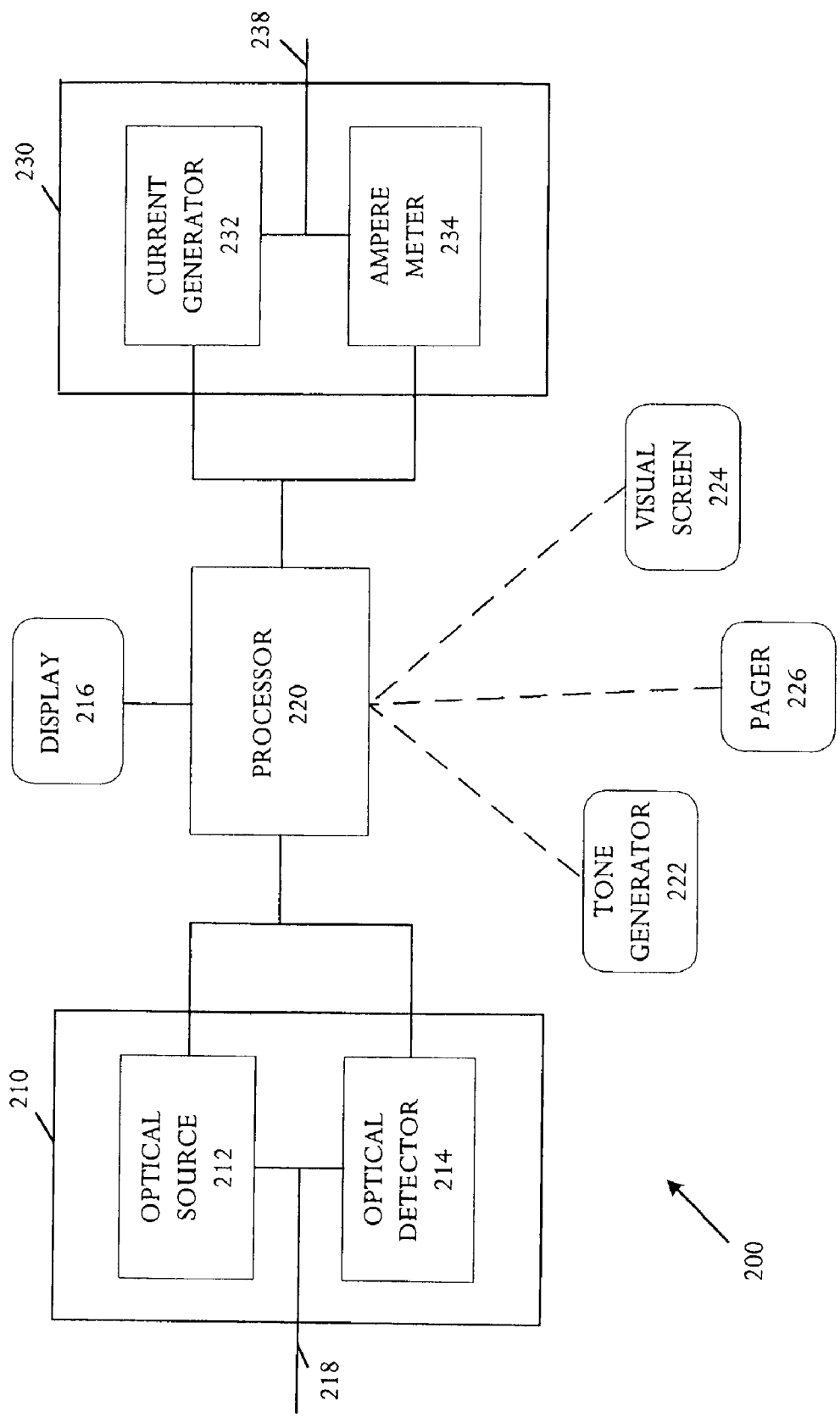
FIG. 2 is a schematic pictorial diagram that illustrates another example of an infusion system with a capability to monitor tissue conditions.

Referring to FIG. 2 in combination with FIG. 1, a schematic block diagram shows functional blocks of a physiological monitoring system 200 for monitoring surface tissue and subcutaneous tissue with a capability to monitor tissue conditions. A tissue contacting section 118 contains a sensor pathway and is attached to a control unit housing 124 by an umbilical cable 126. A fiber optic line 218 runs inside the umbilical cable 126 and is connected through the tissue contacting section 118.

Various types of connectors may be used. Several suitable connector types include zebra connectors, pin connectors, conductive adhesives, a modified EKG snap that can be snapped onto a tail connector, a Ziff connector, and others. Circuit connectors may be connected by an interactive "tail" that exits the dressing either internally or externally. Connections are commonly made by CTR-CTR DuPont® "clincher" or AMP® "multiple-crimp" connector. Interconnection may also be attained using CTRCTR, PC board-mounted, slide-in, pressure connectors, Elastomeric® "zebra-strip" connectors and "Z-axis-only" conductive adhesives. The wide range of connection selections address space and cost constraints.

An optical sensing system 210 includes an optical source 212 and an optical detector 214. The optical source 212 is known to those of ordinary skill in the optics arts and typically includes a time-gating circuit, a pulse synchronization circuit, and a gate switch coupled to an infrared generator. The optical detector 214 is known to those having ordinary skill in the optics arts and includes a photonics detector coupled to a processor 220 via an analog to digital converter. Information from the optical detector 214 can be shown on a display 216 such as a liquid crystal display (LCD) module. Light from the optical source 212 is transmitted to the patient's skin via the fiber optic line 218 and reflections from the skin are transmitted back to the optical detector 214 via the fiber optic line 218. The processor 220 can be connected to an alert tone generator 222 to inform a caretaker or the patient of an alert condition.

In the illustrative system, the processor 220 can communicate with a visual screen 224 and pager 226 that are freestanding. A catheter and cable securement support (not shown) can be attached to the tissue contacting section 118.

A polymer protein coating adhesive, hydrogel adhesives, and conductive ink sensor pathway are applied to the tissue-contacting segment 118. A silver conductive ink adhesive can be applied in a selected configuration.

A caretaker uses the monitoring system 200 by applying the tissue contacting segment 118 to the surface of a patient's skin at one or more monitoring positions, including over the site of intravascular insertion. A catheter and cable securement support is applied on an intravenous catheter used to deliver infusion material into the patient's vascular pathway. The umbilical cable 126 attaches to the control housing unit 124. The caretaker can activate the control unit by actuating an on-off switch (not shown).

The infrared generator sends near infrared signals through the infrared delivery pipeline including the fiber optic line 218. The sensor pathway for the optical light could be clear pipelines or free air. The infrared detector responds to pulse excitations from subcutaneous and surface skin. Signals from the infrared detector are monitored utilizing a multi-gain preamplifier circuit (not shown) connected to the output terminal of a photonics detector. A gate switch (not shown) connected to the output terminal of the multi-gain preamplifier controls sampling of the photonics detector signals. The multigain amplifier circuit connects to an integrator (not shown) to integrate the acquired samples.

A time-gating circuit connected to a switch opens and closes the switch at regular time intervals during signal monitoring. The pulse synchronization circuit connected to the time-gating circuit supplies a signal to the time-gating circuit that indicates when the pulse is expected to arrive at the photonics detector. Data from the optical detector 214 are collected, compared to control information, quantified, and analyzed to determine the presence or absence of conditions that may indicate infiltration and extravasation.

The physiological monitoring system 200 may also include a bio-impedance sensing system 230. The bio-impedance sensing system 230 further comprises a current generator 232 and an ampere meter 234. The current generator 232 sends current through the hydrogel conductive sensor pathway to the tissue while an ampere meter 234 records data using an analog to digital converter (ADC) and sends the information to the processor 220. In another example the conductive pathway can be formed by small conductive silver wires. The processor 220 stores data, compares the data with preset information including threshold and patterns to determine the presence of absence of conditions that may indicate infiltration or extravasation.

The processor 220 combines the bio-impedance and optical information and forwards information on tissue condition by a wireless interface card, for example, to one or more display screens. The display screens may include screens on a pager, a control unit visual display screen, a computer visual display screen and the like. In one example, information can be web enabled and sent via the Internet to a caregiver via personal digital assistant (PDA).

The hydrogel sensor conductive pathway uses adhesives of hydrogel conductive ink 238 to couple the tissue contacting segment 118 to tissue. In a specific example, the adhesive is an adhesive of silver conductive ink.

The monitoring system can be configured as a highly reliable, lightweight, and economical device for monitoring the tissue conditions and identifying complications that may occur during infusion. A caretaker receives useful information to improve quality of patient care in the hospital, home care setting, chemotherapy clinic, or at any location.

Figure 3:
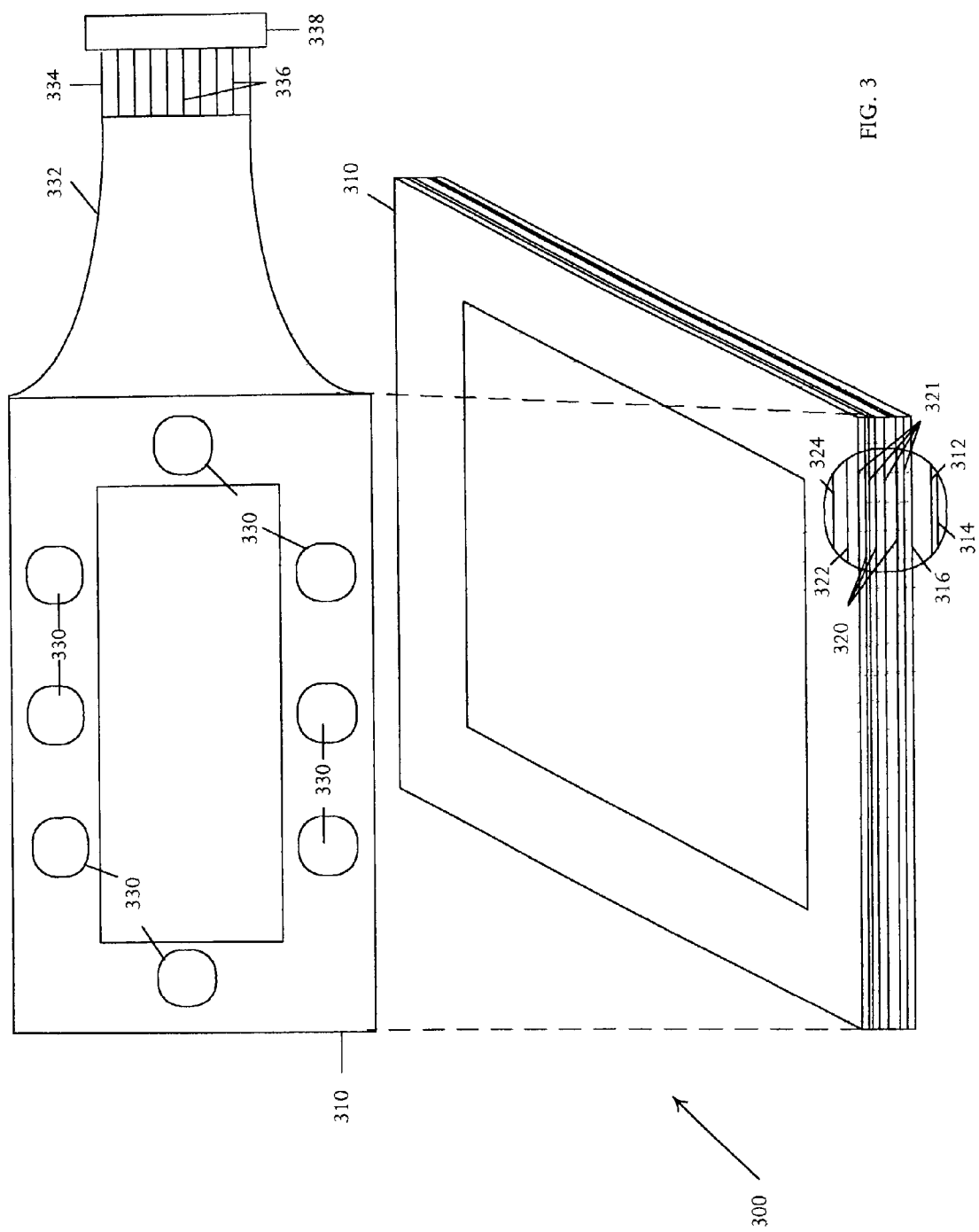
FIG. 3 is a pictorial diagram showing an example of a suitable film barrier dressing for usage with an infusion system.

Referring to FIG. 3, a pictorial diagram shows an example of a suitable film barrier dressing 300 for usage with an infusion system. The film barrier dressing 300 is a flexible membrane can be temporarily attached to a patient's skin and later removed. The film barrier dressing 300 can be constructed from several flexible membrane materials such as breathable barrier films that supply moisture vapor permeability while preventing passage of liquids through the dressing. Typical flexible membrane materials include microporous materials and dense monolithic membranes. Some of the membrane materials are useful for infection control and pass water vapor while excluding or killing pathogenic microorganisms such as bacteria.

A microporous structure has capillary-like pores that inhibit liquid flow due to the small size of the pores and lyophobicity of the polymer membrane material. Gases and vapors permeate a microporous film by physical mechanisms based on pore size. If the diameter of the holes is less than the mean free path of the gas, individual molecules can pass but bulk gas flow is prevented. Physical structure rather than polymer chemistry determines permeability of microporous films, in contrast to dense monolithic membranes.

A dense monolithic membrane functions as an absolute barrier to liquid but has selective permeability to gases and vapors. The dense membranes are pinhole-free polymer membranes that transmit vapors and noncondensable gases through activated diffusion resulting from concentration gradients within the membrane. Suitable polymers include nonpolar, nonhygroscopic polymers such as polyethylene and polypropylene. Permeability is increased for variations in chemistry or structure that increase diffusion constant and permeability.

Suitable barrier membrane materials include film dressings from Tyco Healthcare—U.S. Surgical of Norwalk, Conn., Tegaderm™ and pad transparent dressing from 3M of Minneapolis, Minn., and dressings from Protein Polymer Technologies, Inc. of San Diego, Calif., transparent films that function in the manner of artificial skin. For example, suitable film dressings are secure dressings that are transparent for viewing the puncture site and condition of surrounding skin, while preventing proliferation of bacteria.

The film barrier dressing 300 has a laminar structure comprising, for example, a base film 312, an adhesive layer 314 coupled to an application side of the base film 312 and a foam layer 316 coupled to the base film surface opposite the adhesive. Coupled to the foam layer 316 is a conductive ink layer 320 that is patterned to form electrically conductive lines. In one example, the conductive ink is composed of silver/silver chloride although other conductive materials may be used including carbon, gold, electrically conductive composites, metallics, conductive polymers, foils, films, inks, or any forms of thermistor catheters. Other suitable conductive materials include wires, platinum, aluminum, silicone rubber conductive materials with nickel-graphite compounds, nanopowders and proteins, graphite conductive wires, and the like. A dielectric insulator 321 separates the conductive ink layer 320 in a selective manner and prevents migration of conductive materials.

A hydrogel layer 322 overlies the foam layer 316 and the patterned conductive ink layer 320. A film release liner 324 is coupled to the hydrogel layer 322 for application of the film barrier dressing 300 to the patient's skin. A plurality of electrodes 330 are patterned in the conductive ink and also in conductive portions of the adhesive and integrated hydrogel to make contact with the patient's skin. The conductive ink layer 320 is patterned to form conductive lines in the film barrier dressing 300 that extend to a terminal strip 334 with contacts 336 for connecting to communication lines in a cable for communicating with a control unit. In one example, the control unit communication lines electrically connect to the contacts 336 using a clip 338 containing terminals capable of supplying an energizing signal to the electrodes 330. A connecting pad (not shown) in combination with the dielectric insulator 321 supply insulation and protection against migration of conductive material in the cable containing the conductive circuit and at a junction of the connecting pad and the cable.

In some embodiments, the film barrier dressing 300 utilizes a conductive ink layer 320 in which a silver conductor is cured on a material that can be affixed to tissue. The silver conductor is screen printed on a flexible material. The silver conductor can utilize a polymer thick film composition such as polyester, polyamide, polycarbonate, and epoxy glass. The silver chloride ink is ink printed on the sensor system material.

The film barrier dressing 300 includes a frame 310 and a flexible protective film 332. In the illustrative example, the frame 310 extends along peripheral edges of the film barrier dressing 300 leaving an interior void, and the flexible protective film 332 is attached to the frame 310 and extends over the interior void. The electrodes 330 may be formed in the frame 310, the flexible protective film 332 or both.

The interior void is typically sufficiently large to allow visualization through the patient's skin. The frame 310 can be composed of any material with suitable flexibility, strength, and hygienic properties. A suitable frame material is Melinex from Tekra Corporation of New Berlin, Wis. Although the frame 310 is depicted as rectangular in geometry, any suitable shape may be used including circular, oval, triangular, or any other shape. The electrodes 330 are typically configured as two or more electrode pairs. For example, so that alternating electrical energy may be applied to a first pair of electrodes to generate an electric field to induce a signal in a second electrode pair. The generated field is a function of the impedance of the tissue.

The electrodes 330 can be flexibly formed in various suitable configurations to facilitate detection of selected signals. The electrodes 330 can be patterned in selected shapes by laminating alternating planes of conductive ink layer 320 and layers of dielectric insulator 321. For example, conventional semiconductor laminating techniques can be used to form electrodes 330 of desired geometries. In some particular examples, coil electrodes can be manufactured by selective patterning of multiple layers, with individual layers having a patterned conductive ink layer 320. Overlying and underlying patterns in the conductive ink layer 320 form the coils. Coil electrodes generate a favorable current density distribution for electrical measurements. Coil electrodes commonly interrogate in a frequency range of 1 MHz to 10 MHz to attain good depth sensitivity. In contrast contact electrodes generally operate in a frequency range from about 10 kHz to 100 kHz. In various systems, the coils may have different configurations. Some coils are contact coils that are placed in contact with the skin, other coils are noncontact coils that are removed from the skin by a predetermined distance.

A control unit communicates with the electrodes 330 in the film barrier dressing 300 to gather and process information for determining tissue impedance. The control unit determines the occurrence of extravasation analyzing tissue impedance measurement patterns in time and space, thereby enabling early detection.

In an example of a tissue impedance measuring operation, a caretaker affixes the film barrier dressing 300 so that the electrodes 330 enclose the tip of the needle or catheter and extends up to approximately three inches. The extended film barrier dressing 300 can monitor tissue in the area of the insertion site of the vascular access device and surrounding perivascular tissue. The control unit applies a voltage across a first pair of electrodes to induce a signal in a second pair of electrodes and measures impedance at the second pair of electrodes. The control unit stores the impedance measurements over time and determines changes in the impedance from a baseline measurement taken prior to commencing the injection procedure.

The infusion system is typically used to detect IV complications by introducing a cannula or needle into the patient's vascular system, removing the film release liner 324 and attaching the film barrier dressing 300 to the patient's skin using the adhesive layer 314. The film barrier dressing 300 is positioned so that the needle tip is covered by the void interior to the frame 310.

The film barrier dressing 300 functions as a securement system that is adaptable to cover a suitable size area of tissue. In one example, the film barrier dressing 300 is a flexible material that is adaptable to cover an area of approximately 1×1 inch or extendable to approximately 3×8 inches. Typically, the smaller patch can be used to monitor at the infusion site and the larger patch can be used at any suitable location on the body.

In some embodiments, the film barrier dressing 300 may include a polymer delivery system with a topical antiseptic applied for delivering topical antibiotics. The topical antiseptic is delivered over time with electrical current applied to the electrodes to enhance antibiotic delivery and increase penetration of the antibiotic through the skin.

In a specific example, a dressing may include lidocaine for topical application. In some systems, the antiseptic may be applied to the dressing prior to application to the patient's skin, for example, as a manufacturing step. In other systems, the dressing is applied to the patient's skin without the antiseptic so that baseline sensor measurements may be acquired. The antiseptic may then be applied later to better track changes that result from the therapy.

Figure 4:
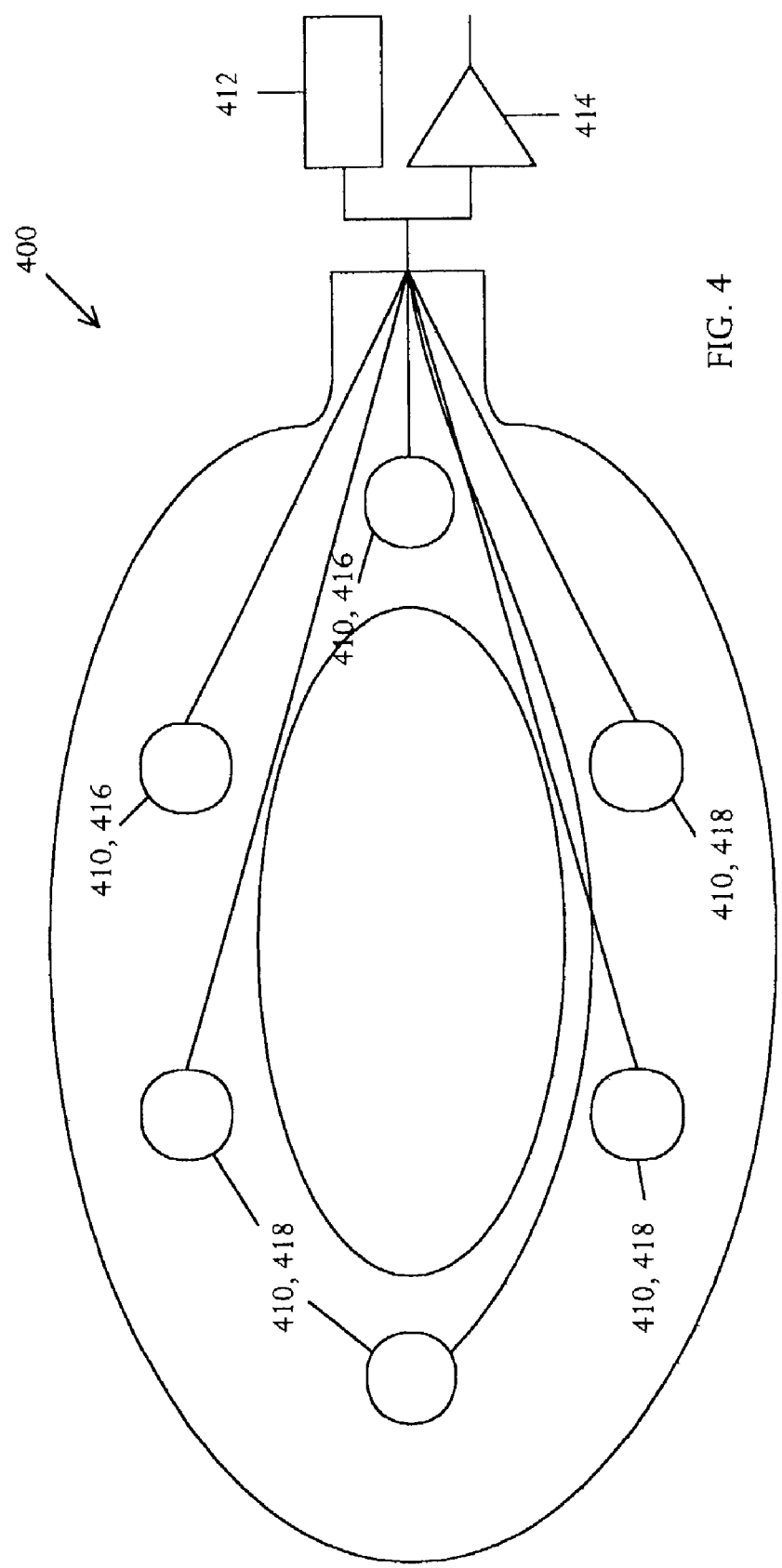
FIG. 4 is a schematic pictorial diagram that illustrates top and cross-sectional views of an example of a suitable electrical impedance sensor for usage in an infusion monitoring device.

Referring to FIG. 4, a schematic pictorial diagram illustrates an example of a suitable electrical signal sensor 400 that is capable of measuring bio-potentials, bio-impedances, electrical impedances, and the like for usage in an infusion monitoring device. The illustrative electrical signal sensor 400 is a plethysmograph that can be applied to a patient's appendage to detect extravasation, infiltration, phlebitis, or other conditions during injection of fluid into the patient's blood vessel. Typically, an electrical impedance sensor 400 is positioned so that the geometric center of multiple sensor elements corresponds to the location of the injection site.

The illustrative electrical impedance sensor 400 has six electrodes 410. Other examples of a suitable sensor may have fewer electrodes or more electrodes. The electrodes 410 may be constructed from a silver/silver chloride mixture or other suitable conductive material. The illustrative electrodes 410 include three stimulating electrodes 418 and three receiving electrodes 416.

The electrodes 410 can be positioned, if possible, in direct ohmic contact with the patient's skin or, otherwise, capacitively coupled with a slight offset from the skin in the vicinity of the injection site.

The electrical impedance sensor 400 includes a current source 412 for applying a current to the injection site via the stimulating electrodes 410 and a high impedance amplifier 414 that is connected to the two receiving electrodes 410 and receives and amplifies the voltage difference between the receiving electrodes 416. The current source 412 typically injects radio frequency (RF) energy in a suitable range of frequencies, for example from one kilohertz to about one megahertz.

Extravasation causes a volume change due to tissue swelling and a conductivity change which, in combination, change the electrical impedance sensed by the receiving electrodes 416. An impedance variation modifies the voltage detected by the high impedance amplifier 414, permitting extravasation detection, notification of IV complications of infiltration, extravasation, and other conditions, and intervention, for example by terminating IV application.

The electrodes 410 can be positioned on the surface of a high dielectric layer (not shown) to attain efficient capacitive coupling to the patient. A hydrogel layer (not shown) coupled to the high dielectric layer on the surface for application to the patient's skin may be used to improve electrical coupling of the electrodes 410 to the patient.

A low dielectric layer (not shown) coats the electrodes 410 and the high dielectric layer and functions as a substrate for applying the electrodes 410 to the patient. A high conductivity layer (not shown) coats the low dielectric layer and functions as a ground plane for the electrical impedance sensor 400 that shields the electrodes 410 from stray capacitance, improving impedance measurement reliability.

Although the illustrative electrical impedance sensor 400 has six electrodes 410, additional electrodes may be added in various configurations to attain additional functionality. For example, the six-electrode electrical impedance sensor 400 may be more suitable for detecting extravasation and infiltration in the vicinity of the infusion site and collection of fluid due to dependent edema. Additional electrodes may be added to detect extravasation and infiltration at a position remote from the insertion, for example due to valve disease or weakening of vessel walls. The additional electrodes in combination with the electrodes 410 may be arranged in various configurations to extend diagnostic performance. Alternatively, additional electrical impedance sensors may be used to detect remote extravasation. For example, the electrodes may be arranged in an annular array configuration or a linear array configuration. In one example, two outer electrodes may be connected as a source and sink of RF current, while any two electrodes positioned between the source and sink can be used to measure current, voltage, or impedance. Switches and processing electronics (not shown) can be used to sample from selected inner electrodes to sense extravasation and infusion at multiple positions along the blood vessels.

In some embodiments, sampling of various positions may be modified over time to sample predominantly in the vicinity of the injection in the early IV stages and to sample to detect remote extravasation in later stages when more likely to occur.

The electrical impedance sensor 400 is useful for monitoring intravascular infiltration and extravasation. Intravascular infiltration and extravasation may alter histological and biochemical tissue conditions in intracellular and extracellular fluid compartments, cell membrane surface area, macromolecules, ionic permeability, and membrane-associated water layers. The histological and biochemical changes within the infiltrated tissue or area of infiltration and extravasation result in a measurable change in tissue electrical impedance.

In some embodiments, the electrical impedance sensor 400 comprises a plurality of transducers to generate one or more sensor pathways utilizing depth-selective sensing of tissue bio-impedance in a desired frequency range. The bio-impedance sensor 400 generates cross-sectional surface measurements and subcutaneous measurements at one or more selected tissue depths by controlling the field extension of the sensor pathway. Interrogation of various depths occurs by sampling at electrodes positioned at multiple locations, using electrodes constructed from various different materials, interrogating using a multiple array transducer configuration, and interrogating at various selected frequencies or with various selected interrogation waveforms.

In a particular example, the electrical impedance sensor 400 fast reconstruction technique applies currents to the body surface and measures resulting surface potentials using a. The fast reconstruction technique presumes that a linear dependence exists between the small deviation in impedance and the corresponding change of surface potentials. The geometry of the internal organs or tissue is known so that initial conductivity estimates are presumed known. A sensitivity matrix encodes the presumed impedance values and conductivity changes are found by inverse-matrix multiplication.

Under processor control, the electrical impedance sensor 400 applies currents to selected electrodes on the body surface and measures resulting surface potential distributions from the electrodes. The sensitivity matrix A describes the dependence between small deviations of conductivity and a change of measured surface potentials according to equation (1) in which $\Delta\sigma$ is the vector of the individual conductivity deviations and $\Delta\phi$ describes changes of measured surface potentials:

$$\Delta\phi = A \cdot \Delta\sigma \tag{1}$$

Knowledge of the sensitivity matrix for a model organ or tissue geometry and electrode arrangement permits determination of conductivity deviations according to equation (2) in which $A^{-1}$ is the pseudoinverse of matrix A determined using singular value decomposition:

$$\Delta\sigma = A^{-1} \cdot \Delta\phi \tag{2}$$

The sensitivity matrix A can be determined by simulating measurements using conductivity values obtained from literature or experiment. In some applications, conductivity values can be gradually changed and surface potential distributions can be measured for the different conductivity values to determine the column values for the matrix. In alternative examples, sensitivity can be directly calculated using a more efficient finite element analysis discussed hereinafter with respect to FIGS. 12 to 17.

The electrode pattern and position are selected for the particular tested organ or tissue, depending on the geometry and conductivity distribution of normal and abnormal tissue, and optimized to generate the maximum voltage difference between the normal and abnormal case.

The electrical impedance sensor 400 includes multiple sets of electrodes and the pattern of excitation current and electrode shape and position is defined based on application. The electrical impedance sensor 400 is configured to recognize objects in a formal known position according to conductivity data measured for normal tissue. Accordingly, test measurements of current density distribution in normal and abnormal cases are stored and compared with test measurements to classify the tissue under test.

Some embodiments may use one large electrode and a plurality of small electrodes. Measurements may be made at one or more test frequencies depending on the impedance frequency spectrum of the measured tissue. Pattern recognition is made based on modeling of electric fields and current density using sensitivity analysis for pattern recognition in three dimensions and finite element analysis. In various embodiments, linear inversion or nonlinear inversion may be used for pattern recognition.

In some embodiments, a control unit obtains and compares the bio-impedance measurements to measurements acquired using a second technology. For example, an optical sensor can be used to detect a light reflection pattern generated by an infrared light source. Other embodiments may use only a single measurement technology.

In another example of a fast bioimpedance tomography technique, tissue impedance maps are constructed from surface measurements using nonlinear optimization. A nonlinear optimization technique utilizing known and stored constraint values permits reconstruction of a wide range of conductivity values in the tissue. In the nonlinear system, a Jacobian Matrix is renewed for a plurality of iterations. The Jacobian Matrix describes changes in surface voltage that result from changes in conductivity. The Jacobian Matrix stores information relating to the pattern and position of measuring electrodes, and the geometry and conductivity distributions of measurements resulting in a normal case and in an abnormal case. The objective of the nonlinear estimation is to determine the maximum voltage difference in the normal and abnormal cases.

In another example of a sensing technology using biopotential measurements, the electrical signal sensor 400 may measure the potential level of the electromagnetic field in tissue. A suitable bio-potential sensor includes a reference electrode and one or more test electrodes. In some systems, the test and reference electrodes may be interchangeable, for example under control of a processor, to vary the desired tissue measurement field.

The sensor may be any suitable form of electrode 410. In one example, the electrodes 410 are predominantly composed of a silver chloride (AgCl) layer coupled to an electrode lead by a silver (Ag) layer. The tissue contact surface of the electrode is a concentrated salt (NaCl) material coupled to the AgCl layer. The electrode may also include an insulated housing that covers the AgCl layer, the Ag layer, and the end of the lead to reduce electromagnetic interference and leakage.

The patient's tissue generates an electromagnetic field of positive or negative polarity, typically in the millivolt range. The sensor measures the electromagnetic field by detecting the difference in potential between one or more test electrodes and a reference electrode. The bio-potential sensor uses signal conditioners or processors to condition the potential signal. In one example, the test electrode and reference electrode are coupled to a signal conditioner/processor that includes a lowpass filter to remove undesired high frequency signal components. The electromagnetic field signal is typically a slowly varying DC voltage signal. The lowpass filter removes undesired alternating current components arising from static discharge, electromagnetic interference, and other sources.

Another example of a sensing technology employs noninvasive depth-selective detection and characterization of surface phenomena in organic and biological material by surface measurement of the electrical impedance of the material where the device utilizes a probe with a plurality of measuring electrodes separated by a control electrode. More particularly, the impedance sensor comprises a measuring electrode 412 structure with triple annular concentric circles including a central electrode, an intermediate electrode and an outer electrode. All electrodes can couple to the skin. One electrode is a common electrode and supplies a low frequency signal between this common electrode and another of the three electrodes. An amplifier converts the resulting current into a voltage between the common electrode and another of the three electrodes. A switch switches between a first circuit using the intermediate electrode as the common electrode and a second circuit that uses the outer electrode as a common electrode.

The sensor selects depth by controlling the extension of the electric field in the vicinity of the measuring electrodes using the control electrode between the measuring electrodes. The control electrode is actively driven with the same frequency as the measuring electrodes to a signal level taken from one of the measuring electrodes but multiplied by a complex number with real and imaginary parts controlled to attain a desired depth penetration. The controlling field functions in the manner of a field effect transistor in which ionic and polarization effects act upon tissue in the manner of a semiconductor material.

With multiple groups of electrodes and a capability to measure at a plurality of depths, the sensor has a capability of tomographic imaging or measurement, and/or object recognition. Other implementations that use fewer electrodes and more abbreviated, fast reconstruction technique of finite-solution pattern recognition, can be constructed in smaller, more portable systems. Conventional tomography techniques are computation intensive and typically require a large computer. Although these computation intensive techniques can be used to implement the disclosed system, other techniques with a lower computation burden may be used, such as the fast reconstruction technique. The fast reconstruction technique reduces computation burden by utilizing prior information of normal and abnormal tissue conductivity characteristics to estimate tissue condition without requiring full computation of a non-linear inverse solution.

Figure 5:
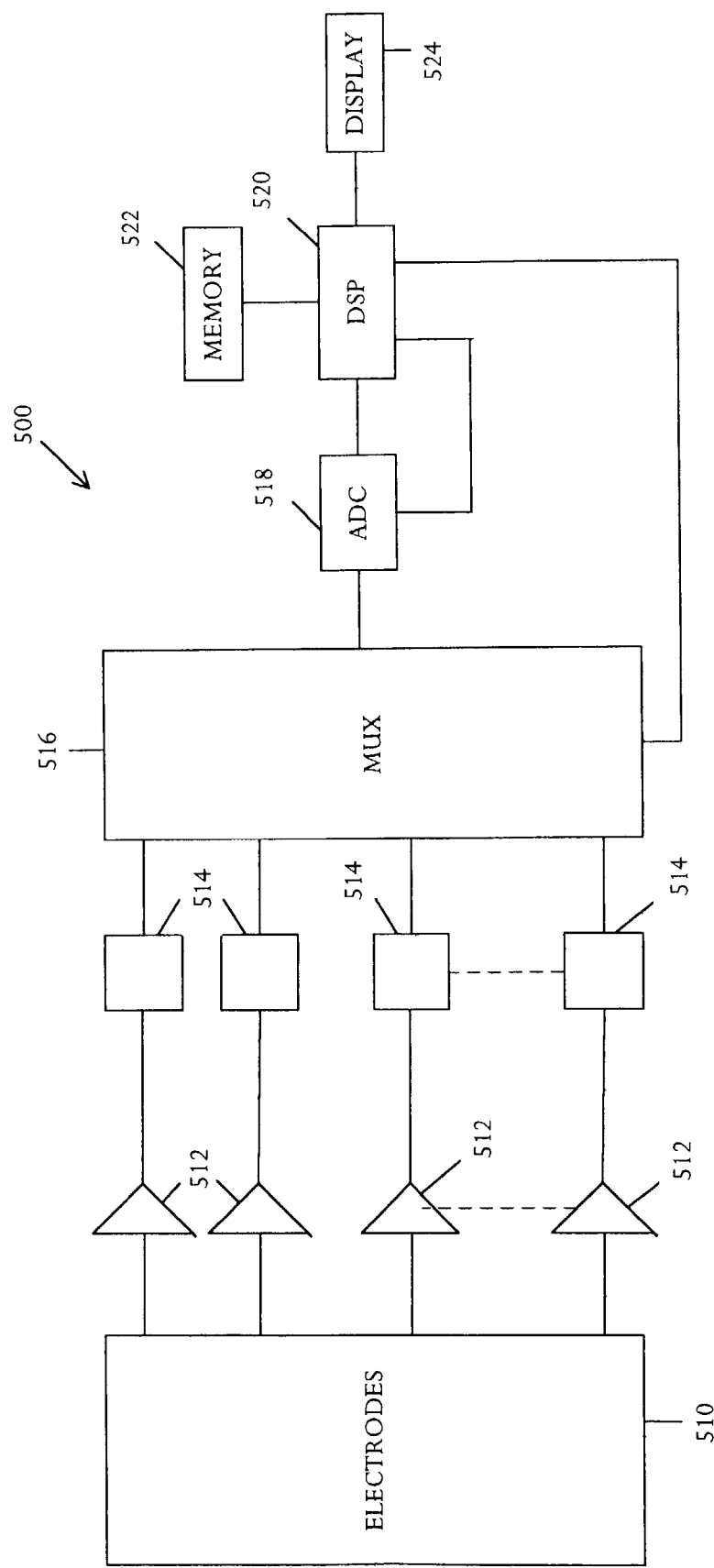
FIG. 5 is a schematic block diagram illustrating another example of an electrical signal sensor in the configuration of an electrode array sensor.

Referring to FIG. 5, a schematic block diagram illustrates another example of an electrical signals sensor in the configuration of an electrode array sensor 500. The electrode array sensor 500 is useful for sensing techniques including impedance, bio-potential, or electromagnetic field tomography imaging of tissue. The electrode array sensor 500 comprises an electrode array 510 is a geometric array of discrete electrodes. The illustrative electrode array 510 has an equal-space geometry of multiple nodes that are capable of functioning as sense and reference electrodes. In a typical tomography application the electrodes are equally-spaced in a circular configuration. Alternatively, the electrodes can have non-equal spacing and/or can be in rectangular or other configurations in one circuit or multiple circuits. Electrodes can be configured in concentric layers too. Points of extension form multiple nodes that are capable of functioning as an electrical reference. Data from the multiple reference points can be collected to generate a spectrographic composite for monitoring over time In an illustrative example, the electrode array 510 is configured to function as one or more measurement channels. An individual channel includes one or more electrodes that supply current to the tissue at a selected frequency and selected waveform morphology. Another electrode in the channel is a sensing electrode that senses the voltage generated.

Alternatively, the array may take any suitable form including a rectangular, square, circular, oval, triangular, or any other two-dimensional shape. The array may include peripheral array elements with central elements omitted, or take any shape with any patterns of inner or peripheral elements omitted.

Electrode spacing configurations are predetermined according to the spatial frequency of the detected electric field potential.

Spatial tomography imaging of tissue using detected electrical parameters generally involves spatial deconvolution of detected signals to reconstruct electrophysiological patterns from detected surface signals.

Individual electrodes in the electrode array 510 are coupled to a signal conditioner/processor including preamplifiers 512 for high gain amplification at high input impedance, low current loading, and low noise. The preamplifiers 512 may be configured to function as a band pass filter or the signal conditioner/processor may include a band pass filter 514 to confine signals to a desired frequency band. Band pass filtered signals are applied to a multiplexer 516 that can be part of the signal conditioner/processor to sequentially sample amplified and filtered analog signals from individual electrodes in the electrode array 510.

Analog signals from the multiplexer 516 are digitized by an A/D converter 518 that sequentially samples signals from the individual electrodes of the electrode array 510.

Digital signals from the A/D converter 518 can be applied to a processor 520 for analysis, storage 522, and/or display 524. The processor can execute a variety of functions such as computing a spatial deconvolution transformation of detected electrode field potentials.

In another example of the electrode array sensor 500, the electrodes can be arranged as one or more sets of electrode groups. An electrode group includes three pairs of electrode. A first electrode pair is excitation electrodes, a second pair is sensing electrodes, and a third pair is focusing electrodes. The focusing electrodes focus current flowing between the excitation electrodes to the sensing electrode region.

The excitation electrodes and the sensing electrodes are spaced so that the sensing electrodes are capable of measuring the voltage drop between the sensing electrodes that occurs as a result of an excitation pulse at the excitation electrodes. The focusing electrodes focus the current flowing between the excitation electrodes to the sensing electrode region. In one example, the focusing electrodes are planar electrodes, aligned and on opposite sides of the line between the two excitational electrodes.

Figure 6A:
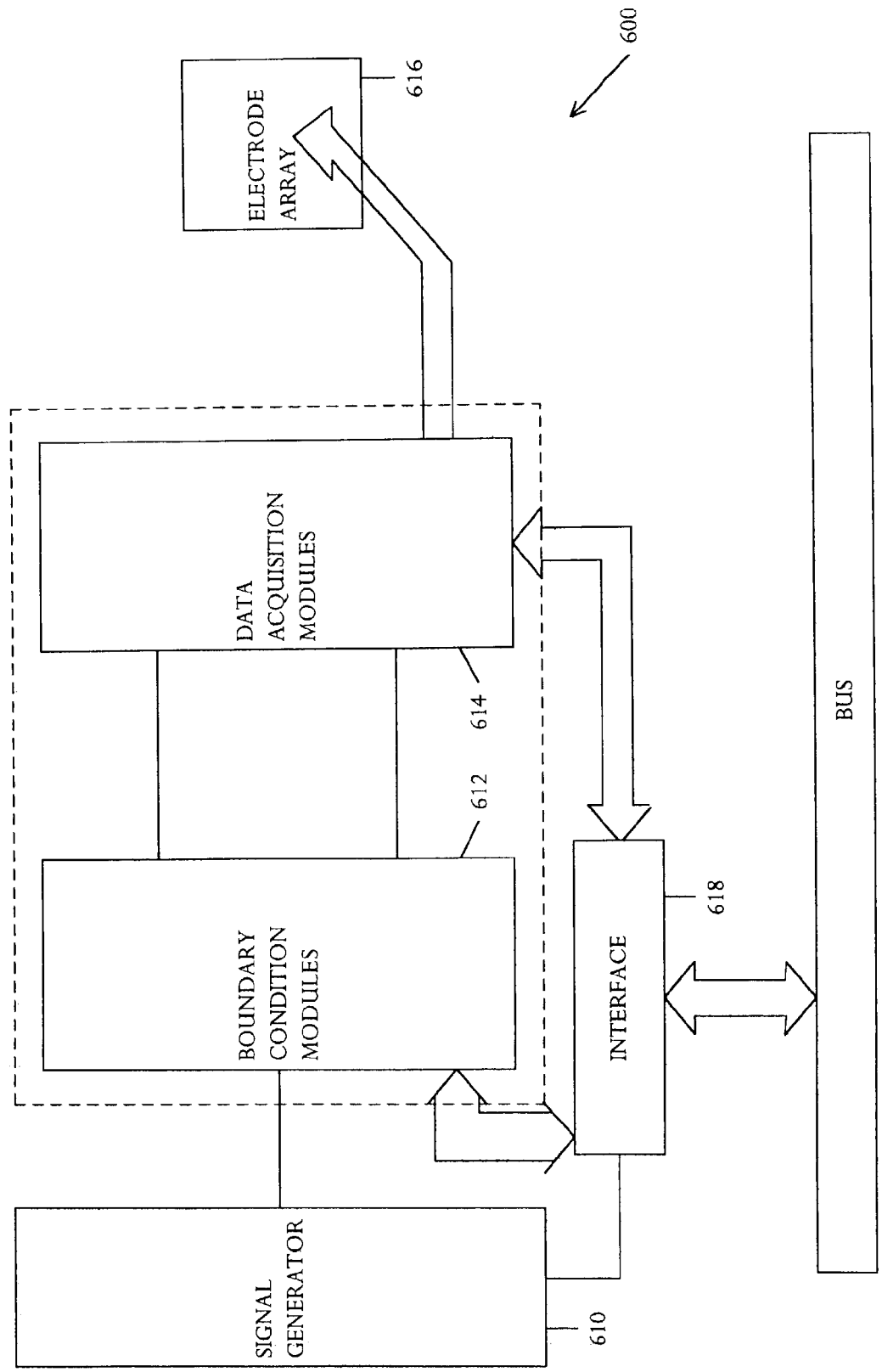
FIGS. 6A and 6B are block diagrams illustrating an example of an additional electrical signal sensing technology, an electric signal tomogram scanner.
Figure 6B:
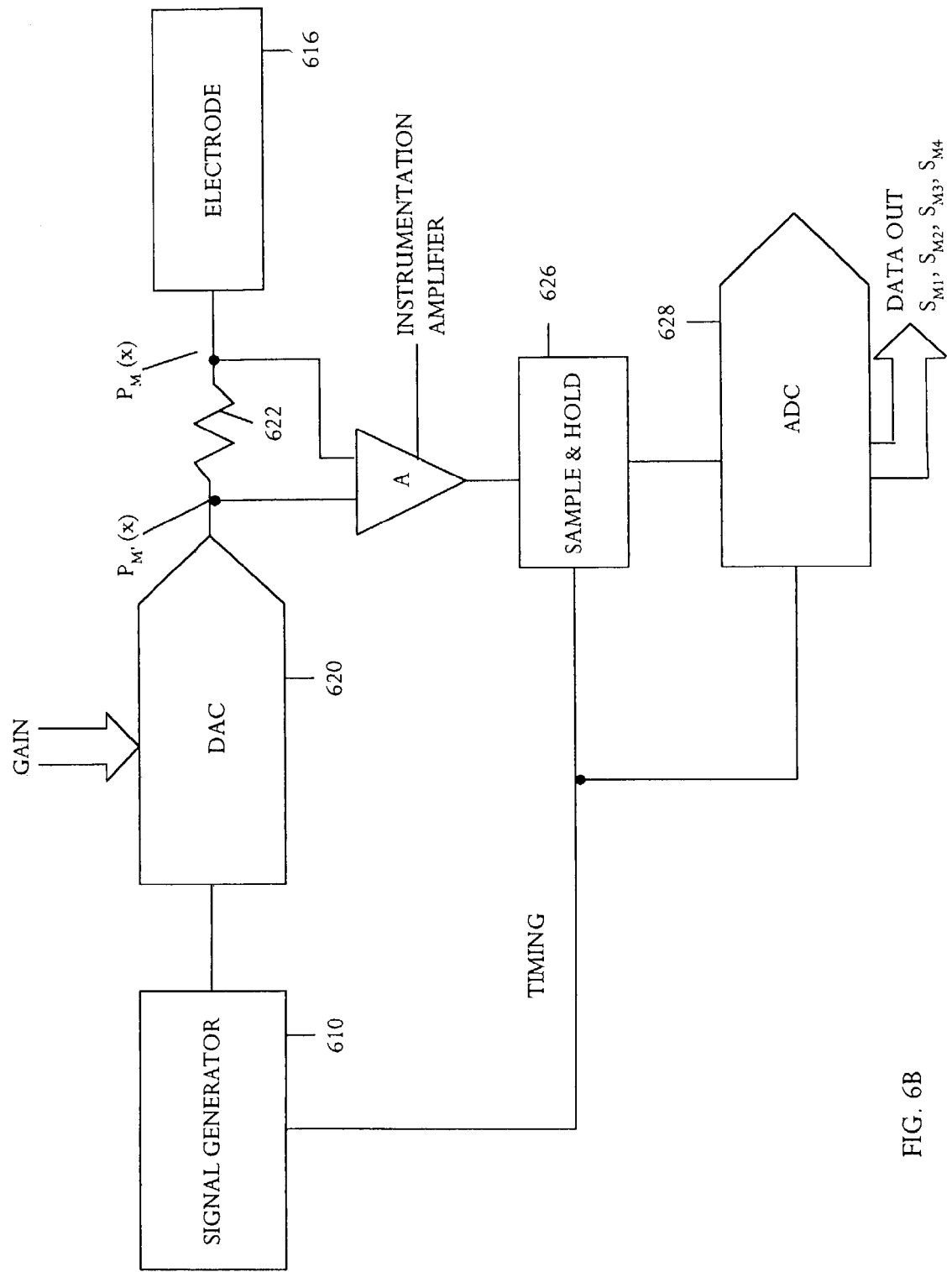

Referring to FIGS. 6A and 6B, block diagrams illustrate an example of an additional electrical signal sensing technology, an electric signal tomogram scanner 600 that may be used in embodiments with extensive computation capabilities. Other implementations that use more abbreviated fast reconstruction technique of pattern recognition, can be constructed in smaller, more portable systems. The electric signal tomogram scanner 600 comprises a signal generator 610, a plurality of boundary condition modules 612, a plurality of data acquisition modules 614, and an electrode array 616. The electric signal tomogram scanner 600 receives control signals from a processor via an interface 618. The signal generator 610 supplies signals to the boundary condition modules 612 that communicate with corresponding data acquisition modules 614 to drive the electrode array 616. A data acquisition module 614 drives a plurality of electrode elements in the electrode array 616. A particular combination of a boundary condition module 612 and a data acquisition module 614 generates boundary conditions and measures resultant voltage drops across small sensing resistors (not shown) to measure electrical signals at the individual electrodes in the electrode array 616.

The signal generator 610 supplies a sinewave voltage of suitable frequency, for example between 100 Hz and 1 KHz to a multiplying digital to analog converter (DAC) 620, generating a voltage drop across resistor 622 and instrumentation amplifier 624 in a data acquisition module 614.

In one example, the signal generator 610 comprises a crystal-controlled oscillator (not shown) coupled to a frequency divider (not shown) that reduces the oscillator frequency. The frequency divider is in turn coupled to a phase splitter (not shown) that produces a further divided signal as one-quarter cycle displaced square waves. The phase splitter supplies the quarter-cycle displaced square wave signals to a delay line (not shown) and to a high Q bandpass filter (not shown). The bandpass filter is coupled to a buffer amplifier (not shown) to generate a sinewave signal p sin 2ft where f is the square wave frequency. An in-phase squarewave, a quadrature squarewave and subconjugates are delayed by the digital delay line to compensate for delay through the bandpass filter and the buffer amplifier. Four phases of the sinewave occur at positive transitions of the squarewave signals and passed to the interface 618.

A sample and hold circuit 626 receives the amplified signal and supplies samples to an analog to digital converter (ADC) 628, timed according to clock signals from the signal generator 610. ADC 628 supplies digital signals indicative of current measurements at the electrode in the electrode array 616.

Electrodes receive a boundary condition that establishes a voltage across the resistor 622. The data acquisition modules 614 first produce a controlled voltage at electrodes in the electrode array 616 to establish a boundary condition, then measure resulting voltages to enable boundary current computation.

In some embodiments, a processor controls the electric signal tomogram scanner 600 to apply a voltage distribution over some external boundary of an object and find the current flow at the boundary from a solution of Laplace's equation to reconstruct the distribution of electrical properties within the object. The process involves positioning a three-dimensional electrode array 616 about the object, applying selected voltages to a selected first set of electrodes and measuring currents through a selected second set of electrodes, which may include some or all of the first set.

The electric signal tomogram scanner 600 imposes a virtual three-dimensional grid onto the object at a selected resolution level with each node of the grid allowed to assume an independent electrical parameter. The scanner determines a best value for the electrical parameter for each node without any preconditions. The electric signal tomogram scanner 600 then performs an iterative process to determine a specific distribution of electrical properties at the grid nodes to most closely match the measured currents at the boundary and the currents based on the specific distributions.

In the illustrative electric signal tomogram scanner 600, the boundary condition modules 612 and the data acquisition modules 614 are identical except that the boundary condition modules 612 store preset boundary conditions in a nonvolatile memory.

Figure 7:
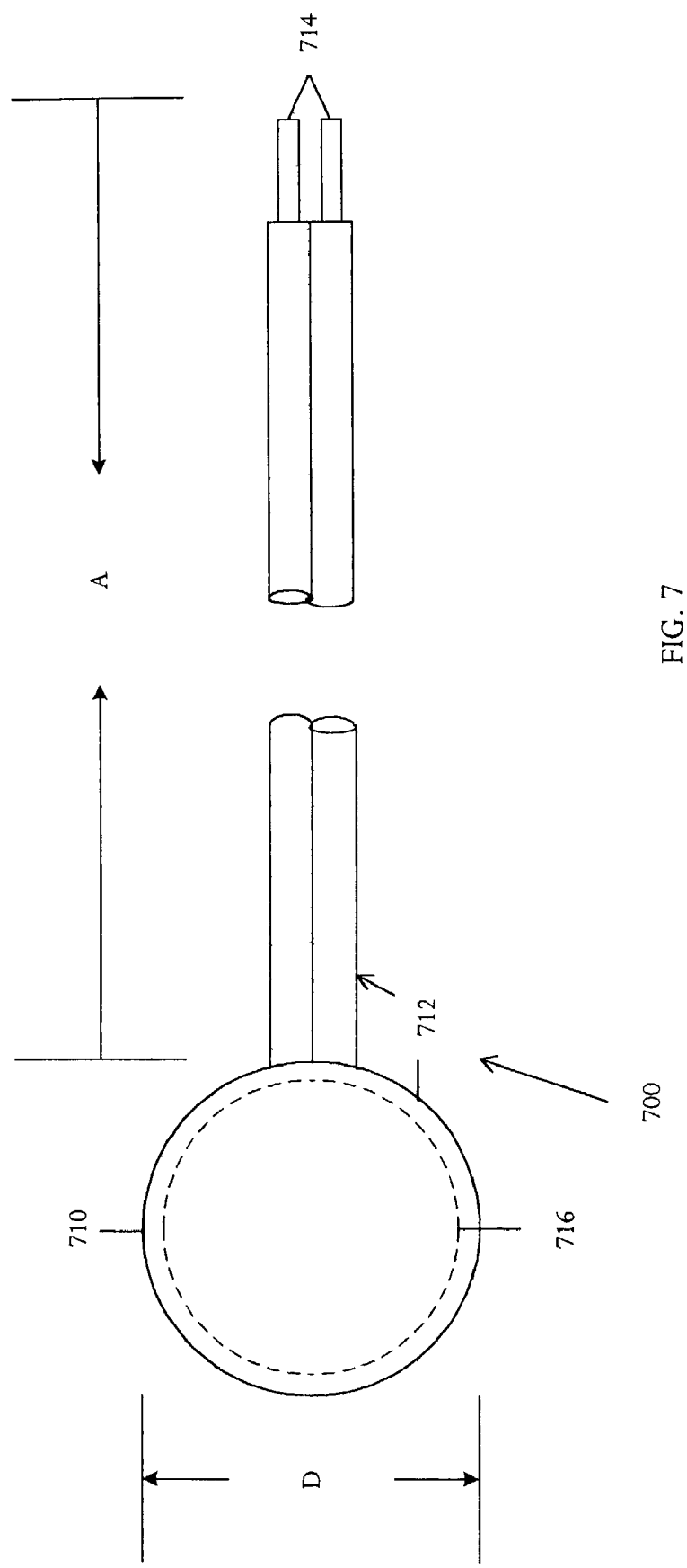
FIG. 7 is a schematic pictorial diagram showing an example of a suitable temperature sensing device for usage in the infusion system.

Referring to FIG. 7, a schematic pictorial diagram shows an example of a suitable temperature sensing device 700 for usage in the infusion system. The illustrative temperature sensing device 700 is a biomedical chip thermistor assembly that is useful both for intermittent and continuous monitoring. The thermistor 700 includes a stainless steel housing 710 that is suitable for reusable and disposable applications and has a nominal resistance value that ranges from approximately 2000 Ω to about 20,000 Ω at 25° C. The thermistor body 712 including wires 714 and sensor tip 716 can be composed of stainless steel. The wires 714 are insulated using a suitable material such as medical grade PVC teflon. In other examples, the body material can be composed of materials such as lexan for the wires 714 or shaft and an aluminum tip, or molded plastic or kapton. Other suitable insulating materials include teflon, heavy isomid, or polyurethane with a nylon coat. The thermistor 700 is an electrical circuit element that is formed with semiconducting materials and is characterized by a high temperature coefficient. The thermistor 700 functions as a resistor with a temperature coefficient ranging typically from about −3 to −5%/° C. The thermistor can be activated using either current or voltage excitation. The thermistor 700 is connected via the wires or shaft to a high resolution analog to digital converter. Thermistors are non-linear devices so that linearization techniques are typically used to obtain accurate measurements.

Figure 8:
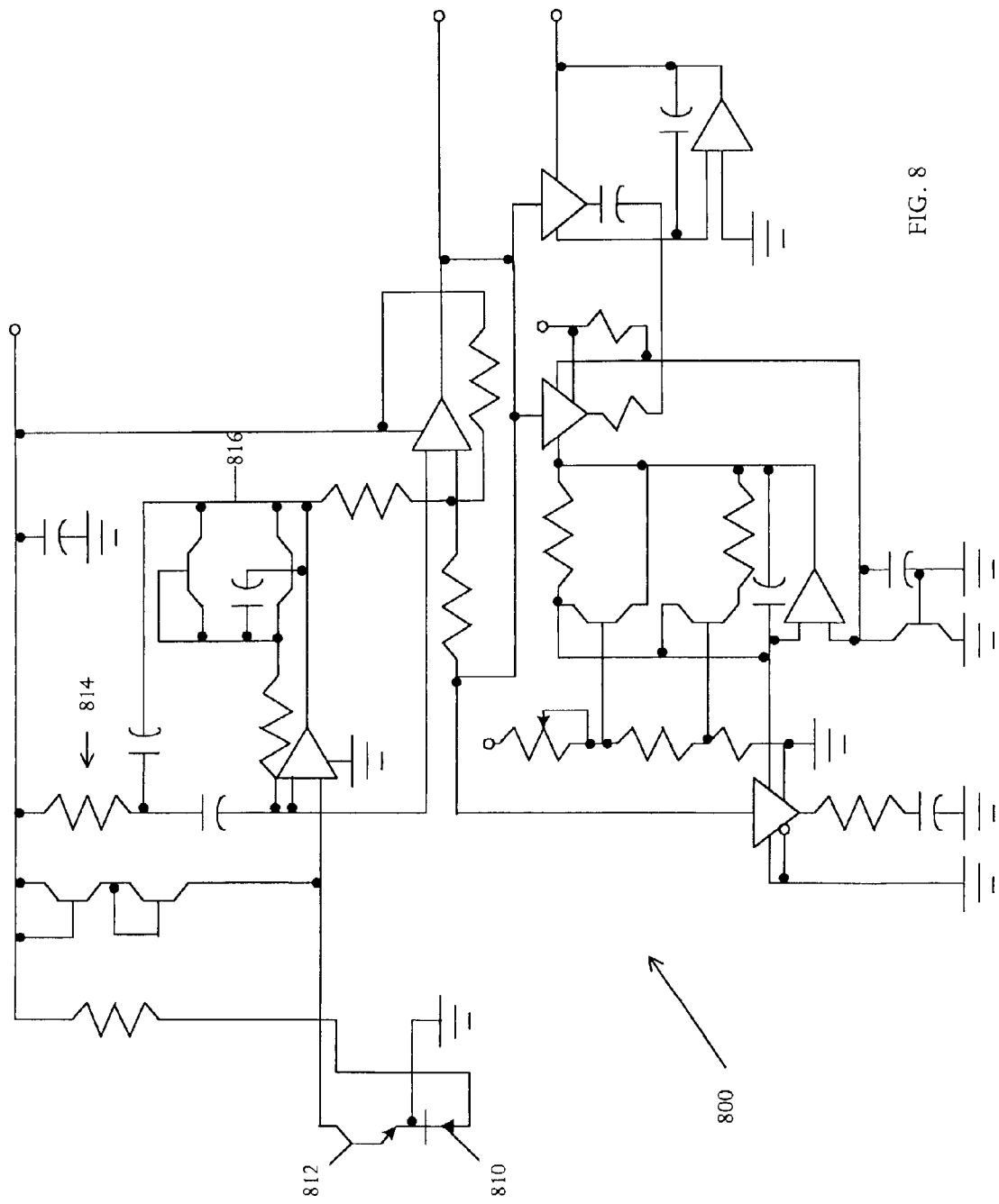
FIG. 8 is a schematic pictorial diagram that depicts a suitable optical sensor for usage with the infusion system.

Referring to FIG. 8, a schematic pictorial diagram depicts a suitable optical sensor 800 for usage with the infusion system. In one example, the optical sensor 800 is an infrared light emitting diode (LED)/phototransistor pair that can sense detectable variations in skin characteristics. The optical sensor 800 comprises an emitter or infrared transmitter (LED) 810 and a photonics or retrosensor detector 812 that measure light reflections to derive data points. When gently pressed against the skin radiation from the transmitter 810 through a cross-section of tissue including surface and subcutaneous tissue reflects back into the detector 812. Retrosensor detector 812 photocurrent detects the infrared signal and produces an ac signal across transistors Q2 and Q3 of about 500 uV peak to peak for a 1% change in skin reflectance, a logarithmic relationship that is constant over many orders of photocurrent magnitude. Therefore reliable circuit operation is possible despite wide variation in skin contrast and light level. Signals from the transistors Q2 and Q3 are applied to a high-gain adaptive filter 814 that rejects ambient optical and electrical noise and supplies a clean signal to comparator 816 to extract a digital signal.

Figure 9:
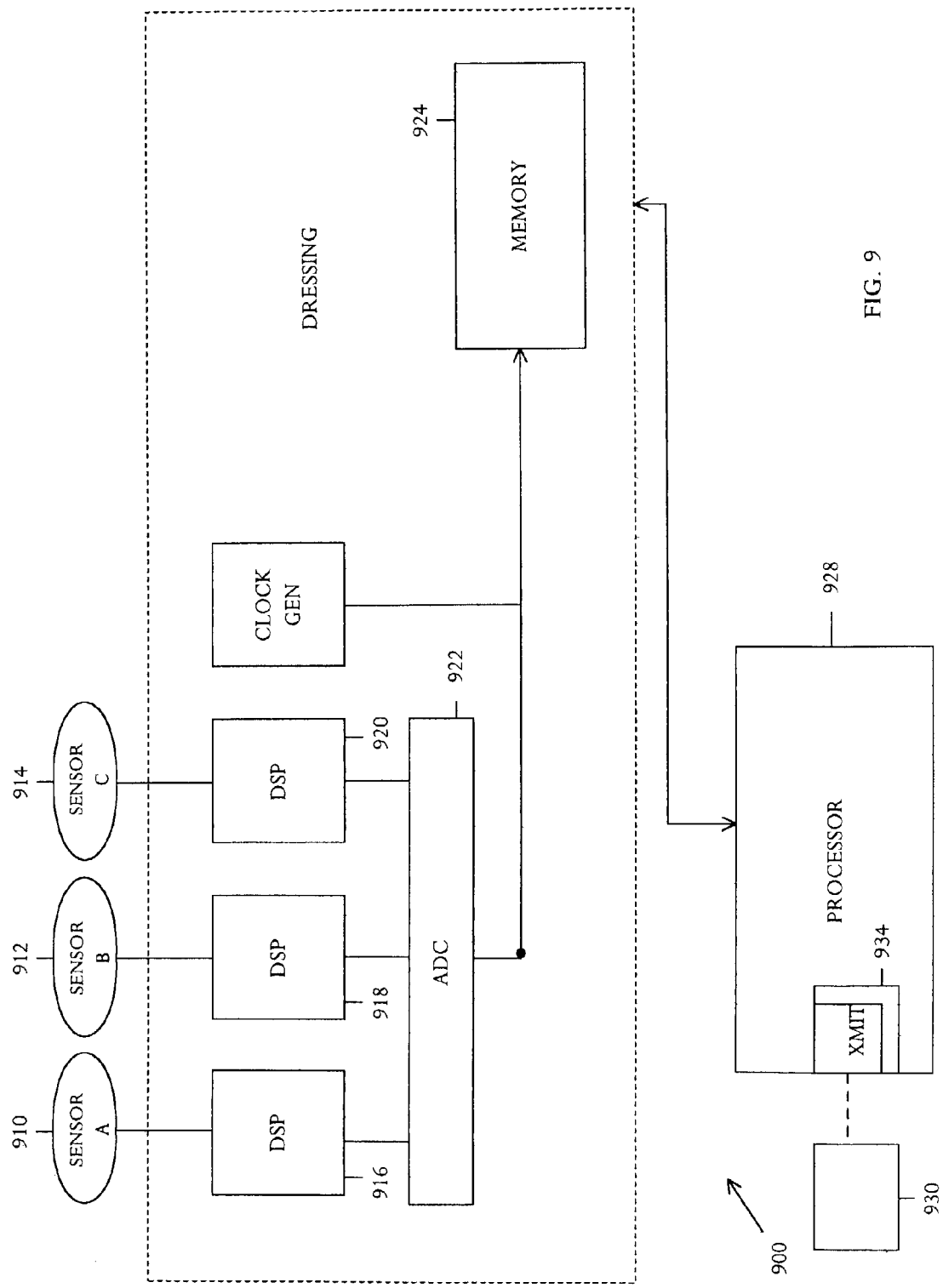
FIG. 9 is a schematic block diagram illustrating an example of a control unit suitable for usage with the illustrative infusion system.

Referring to FIG. 9, a schematic block diagram illustrates an example of a control unit 900 suitable for usage with the illustrative infusion system. The control unit 900 is contained in a housing (not shown) and attaches to one or more sensors 910, 912, and 914 for detecting various physiological signals. Although the illustrated example depicts three sensors, a single sensor or any suitable number of sensors may be implemented depending on the particular parameters to be sensed for an application. One example of a suitable system includes a bio-impedance sensor 910, an optical sensor 912, and an ultrasound sensor 914. Other types of sensors may replace the illustrative sensors or be used in addition to the illustrative sensors. Other suitable sensors include, for example, a flow sensor that senses infusion fluid flow, a pressure sensor, a thermistor, thermometer or other temperature sensing device.

In some embodiments, biosensors can be incorporated into layers of the flexible dressing material. For example, Dupont Microcircuit Materials of Research Triangle Park, N.C. Biosensor materials can be incorporated into the flexible dressing material layers in various geometries using screen printing of conductive inks. Note that other embodiments may utilize more conventional die-cut foils. The conductive inks are highly suitable and permit high-speed, high-volume production using commercially-available production equipment.

The conductive inks are typically silver, gold, and carbon inks composed of thermoplastic polymer-based materials that are screen printed and dried or cured. When the ink is dried and all solvent is removed, the printed area becomes electrically conductive or insulative. The inks carry electrical current from a power supply to an active area of the biosensor. Cured inks have useful properties of low resistivity and thus high conductivity permitting low voltage applications, flexibility, and adhesion.

Because the different inks have varying resistivities, for example gold having a lower resistance than silver, which has lower resistance than carbon, the inks can be selected to achieve selected circuit performance. Carbon ink can be used as an overprint for silver inks to prevent silver migration from two adjacent traces that carry different amounts of current or potential, achieving a battery effect.

The conductive inks are highly adhesive to various substrate materials such as polyester, or Cetus fabric, a polyester substrate supplied by Dynic USA Corporation of Hillsboro, Oreg. Cetus is typically a white backing material for the flexible dressing, upon which silver conductive ink can be printed. Other suitable substrate materials include Polyester, Mylar or Melarax. Printable inks are suitable for usage on a polyester substrate that is print-treated and heat-stabilized.

Polymer thick film (PTF) inks contain a dispersed or dissolved phase and attains suitable final properties simply by drying. When printed and cured on a substrate, a particular electronic or biological functionality develops in the dried film. Suitable substrate include polyester films such as DuPont TeijinT Mular® or Melinex®, or ceramic Green TapeT. PTF products applied to flexible substrates are compact, lightweight, environmentally friendly, inexpensive, and permit efficient manufacturing techniques. PTF films can be folded, twisted, bent around corners, or bonded to any surface, permitting flexible application. PTF films are suitable for small features and layers can be printed in layers to develop multiple functions. Polymer thick film technology is highly suitable for printing electrodes and other components of disposable biosensors.

The conductive inks are flexible to prevent creasing that can increase electrical resistance or cause cracking or delamination of the dressing when stretched. The flexible dressing material in combination with the conductive ink conforms to the body and allows stretching without breaking the electrodes or increasing electrical noise.

Silver/silver chloride (Ag/AgCl) inks are used to deliver drugs or anesthetic through the skin using iontophoresis. The resistance of silver/silver chloride inks used for the electrodes is typically selected to be higher than the silver inks used for electrical connections to restrict the current flowing through the electrodes to low levels suitable for iontophoresis and to facilitate control of iontophoresis. Printing selected amounts of the ink directly over silver traces controls the resistance of silver/silver chloride inks. The desired surface area, iontophoresis rate, and duration of drug delivery are taken into consideration in selection of the size and thickness of Ag/AgCl traces. The stability and reactivity of the drug and/or size of the drug molecule determine applicability for iontophoresis since interstitial areas between skin cells can only be expanded to a limited point with electrical current before irritation occurs.

Other sensors, ampermetric sensors, can be incorporated into the flexible dressing to measure concentration of various substances such as glucose, carbon dioxide, oxygen, and others. For example, a glucose sensor incorporates an enzyme into the dressing that reacts with extracted metabolic analytes such as glucose. The reaction creates a small electrical charge that is proportional to the metabolic reaction rate. An electrode indicates the electrical charge and a sensing circuit converts the electrical charge to a numeric value that can be displayed, analyzed, stored, or the like. The flexible dressing typically includes a hydrogel that stores the enzyme or reagent. The sensor can function using reverse iontophoresis in which silver (Ag) ions move from anode to cathode extracting the metabolic analyte from the body and collected in a hydrogel pad. An electrode, for example a platinum-based electrode, can be used to read the current and function as a catalyst to drive the reaction between enzyme and glucose. Some ion-selective permeability inks also include a carbon component.

Other sensors, for example potentiometric sensors or electrochemistry sensors, can be used to test electrolytes for example potassium (K) and other selective ions. Inks for sensing electrolytes typically include carbon with a platinium catalyst reagent as an ion selective sensor. Potentiometric sensors measure the voltage gradient across a metabolic sample according to the sample's level of conductivity at a selected voltage according to a calibrated standard. The lower the conductivity of the sample, the higher the voltage for delivering a particular fixed current. Some potentiometric sensors use an ion-selective membrane ink printed over the electrodes to filter other analytes that contribute to high background noise.

Dielectric or encapsulant inks are insulators that protect adjacent traces from short-circuiting. The dielectric or encapsulant inks also assist adhesion. Some dielectrics can be used as capacitors to create circuits in combination with resistors formed by various resistive inks inside the dressing. Capacitors within the dressing facilitate storage and release of electric current pulses. Ultraviolet dielectrics can be used to define active sensing areas of an electrode, limiting the surface area of blood or analyte to a selected size.

In other examples, the sensors may include biosensors composed of nanostructured porous silicon films. Film biosensors detect analyte binding processes using a silicon-based optical interferometer. The nanostructured porous silicon films are prepared by an electrochemical etch of single crystal silicon substrates. The biosensor samples are prepared so that the porous silicon films display Fabry-Perot fringes in their white-light reflection spectrum. Biological molecules are chemically attached as recognition elements to the inner walls of the porous silicon matrix. The film is exposed to a complementary binding pair, causing binding and resulting in a shift in Fabry-Perot fringes. Analyte binding may be indicative of infiltration or extravasation.

The individual sensors 910, 912, and 914 may be connected with corresponding respective signal conditioners or processors 916, 918, and 920 in the control unit 900. In the illustrative example, the bio-impedance sensor 910 is coupled to a bio-impedance signal conditioner/processor 916, the optical sensor 912 is coupled to an infrared signal conditioner/processor 918, and the ultrasound sensor 914 is coupled to an ultrasound signal conditioner/processor 920. Although the illustrative example, depicts sensors that are respectively coupled to particular signal conditioners or processors, in other examples two or more sensors may share a particular signal conditioner/processor. In some examples, a signal conditioner/processor may be dedicated to a particular sensor and also use other signal conditioners/processors that may be shared among sensors. For some sensors, the signal from the sensor is suitable without processing or conditioning so that no signal conditioner/processor is utilized.

In the illustrative example the sensors 910, 912, and 914 and the signal conditioners or processors 916, 918, and 920 are analog sensors and conditioner/processors so that the signals from the signal conditioners or processors 916, 918, and 920 are applied to an analog to digital (A/D) converter 922 to convert the analog signals to digital form. In other examples, one or more of the sensors or conditioner/processors may generate digital signals, bypassing the A/D converter 922. The signal conditioners or processors 916, 918, and 920 may include or omit various elements such as amplifiers, filters, switches, and the like.

Digital signals from the A/D converter 922 and/or one or more of the sensors 910, 912, and 914 may be stored in a memory 924 and/or other storage device, or supplied directly to a processor 928, for example under control of the processor 928 or controlled remotely from a remote control and communication device (not shown). Alternatively, signals from the A/D converter 922 and/or the sensors 910, 912, and 914 may be communicated to a remote receiving device 930 via a transmitter/receiver 934 for storage or analysis. Any suitable storage device 924 may be used such as semiconductor memory, magnetic storage, optical storage, and the like.

The memory can also be used to store various sensor and control information including historical information and current information acquired in real time.

In some examples, the control unit 900 may include a clock generator to supply a digital clock signal to correlate signals from the sensors 910, 912, and 914 to time. The A/D converter 922 and/or the sensors 910, 912, and 914 supply signals for storage or analysis at a suitable frequency. For many sensors, a suitable sample frequency may be in a range from 1 to 100 Hertz, although lower or higher sample frequencies may be used. A suitable sample frequency is defined to be sufficiently above a Nyquist sample rate of all signal frequencies of interest.

The processor 928 may be any suitable processing device such as a controller, a microcontroller, a microprocessor, a central processing unit (CPU), a state machine, a digital logic, or any other similar device. The processor 928 typically executes programs, processes, procedures, or routines that control various aspects of signal acquisition, analysis, storage, and communication. The processor 928 is powered by a power source 906 that also supplies energy to other components inside the housing 908 and to the sensors.

The filtered signal is input to the A/D converter 922 to convert the signal to a form usable by the processor 928. Processor 928 performs operations that convert the digital signal to one or more of several useful parameters indicative of the electromagnetic field. In one example, the processor 928 can sum the normalized values of the digital signals to generate an average or mean signal or determine changes in polarity of the signal. The processor 928 can determine a plurality of parameters, analyze the interrelationship of two or more parameters, detect variations of parameters over time, and the like.

The processor 928 acquires a plurality of electromagnetic field samples for a period of the electromagnetic field, and normalizes and sums the values to compute an average or mean value for the period.

Figure 10:
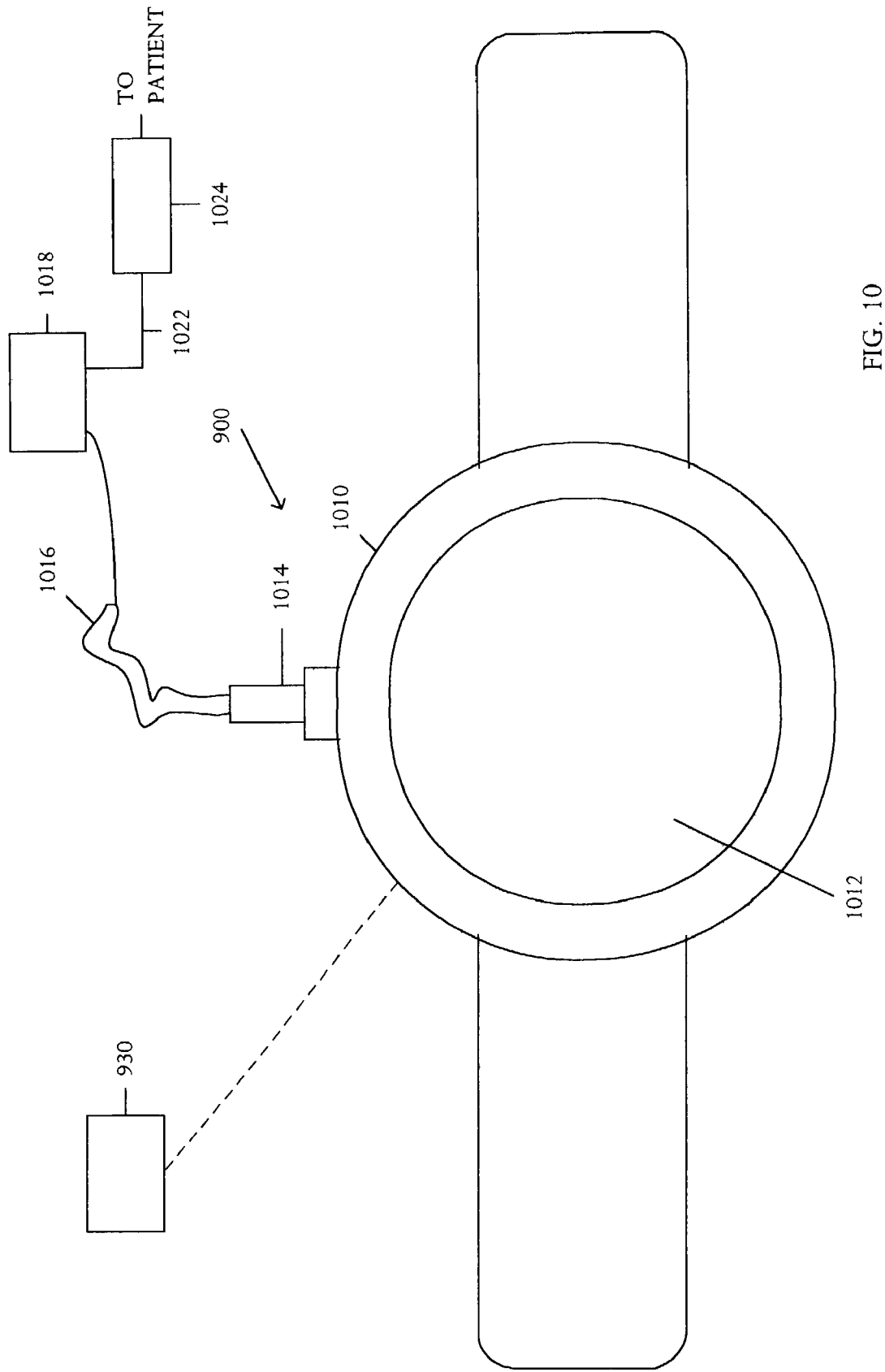
FIG. 10 depicts a schematic pictorial view of an example of a control unit that is configured to be attachable to a patient's arm, IV pole, or other patient's appendage.

Referring to FIG. 10, a schematic pictorial view shows an example of a control unit 900 that is configured to be attachable to a patient's arm or leg for monitoring of extravasation, infiltration, phlebitis, and other conditions during infusion therapy. The control unit 900 performs operations including measurement control, information processing, data storage, and display of results. In some applications, the control unit 900 may process data in real time or may collect data for subsequent analysis.

In the illustrative example, the control unit 900 is housed in a case 1010 a suitable size for attachment to a patient's arm or leg, taped to an alternative portion of the body, or mounted onto an IV pole. The control unit 900 has a visual display 1012 to facilitate viewing by the patient, health care provider, or others. The visual display 1012, for example a liquid crystal display, a computer screen, a personal digital assistant (PDA) screen, a pager visual screen, cellular phone display screens, or any other suitable display. The display 1012 can display various information including results and indications derived from sensor information, alert notifications, current time and date as well as time and date of pertinent events. The visual display 1012 can also display time and date of past and upcoming infusions. The control unit 900 may have an alarm that generates a notification signal such as an audio alarm, vibration, illumination signal, or other suitable types of enunciator.

The control unit 900 stores and compares various types of information to diagnose tissue condition. One or more of various types of data can be stored, compared, and analyzed, for example including current data, reference data, baseline data, information trends, preset parameters, automatic comparison results, patient condition information for disease condition adjustments, environment information, cannula position and motion information, and infusion flow information.

In some embodiments, the case 1010 may include an inlet fluid conductor 1014 that is capable of connecting a proximal conduit 1016 to an intravenous fluid source 1018 such as a syringe, a pump, or an IV bag. An outlet fluid conductor 1020 connects a distal conduit 1022 to an intravenous discharge device 1024 that discharges fluid into a patient's blood vessel.

Information stored in the control unit 900 may be visually presented on the visual display 1012 and/or communicated to a remote receiving device 930 via a transmitter/receiver 934 for storage or analysis. The transmitter/receiver 934 may be either a hardwire or wireless device.

Figure 11:
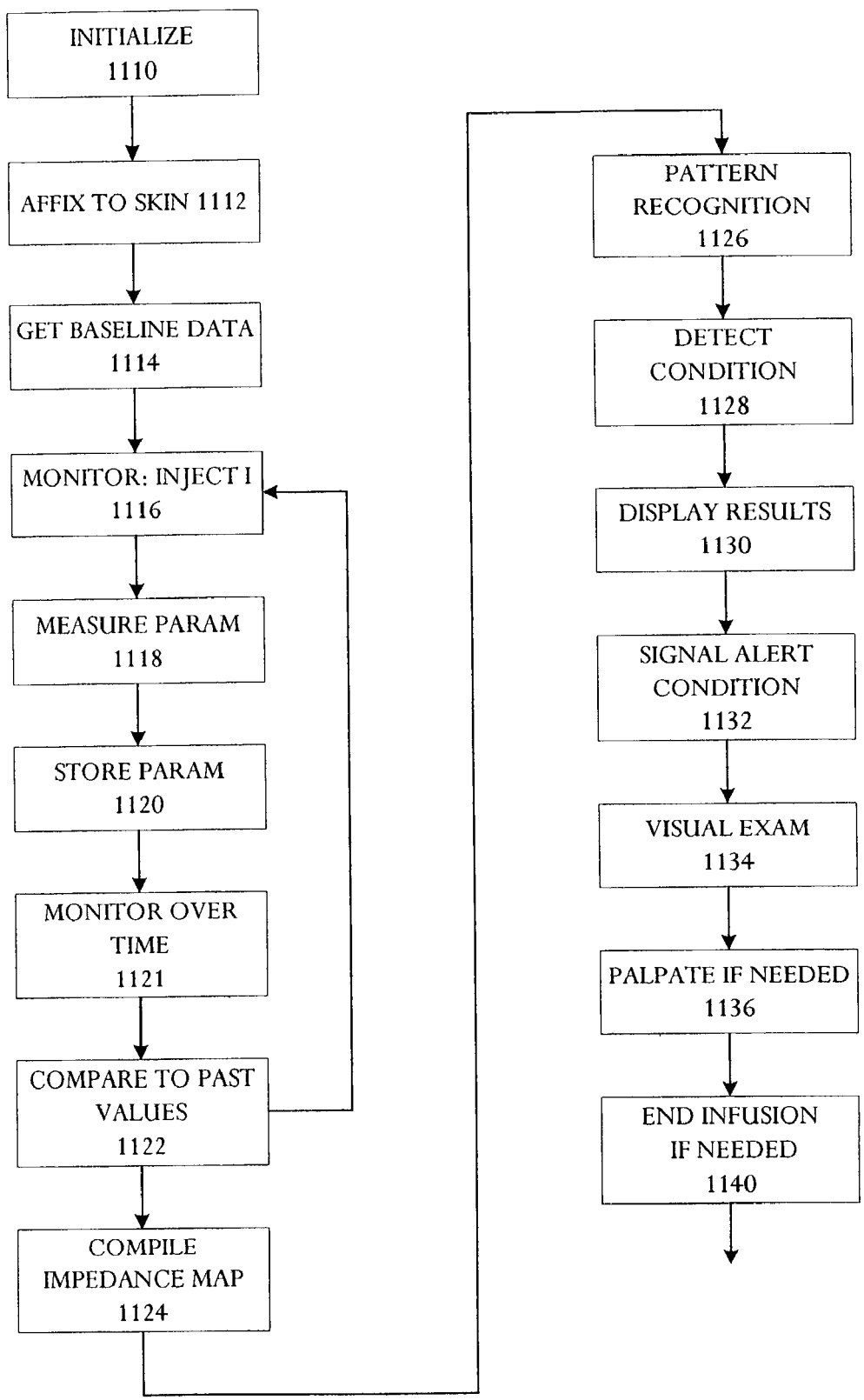
FIG. 11 is a flow chart that depicts an example of a technique for detecting a harmful tissue condition during an infusion.

Referring to FIG. 11, a flow chart depicts an example of a technique for detecting a harmful tissue condition, for example intravascular infiltration, intravascular extravasation or tissue necrosis, during infusion. In an initialization operation 1110 prior to infusion initiation, a film barrier dressing with sensors is affixed to the skin 1112 to one or more sites including the proposed vascular insertion site of a needle or cannula into the vascular pathway. Interconnect lines are connected from the film barrier dressing sensors to a control unit. Additional sensor dressing may be applied to other locations at risk for complications.

The sensors are capable of interrogating the tissue and receiving tissue condition signals using one or more sensing technologies. Suitable sensing technologies may include bio-potential, bio-impedance, photonics, optical sensors, acoustic, ultrasound, and others. In one example, a photonics detector has an infrared generator and a photonics detector. The infrared generator produces a beam of light that scans the surface skin and subcutaneous tissue during monitoring, causing the photonics detector to generate a pulse signal that can be analyzed to determine tissue condition.

The infusion system begins monitoring prior to insertion to obtain baseline pre-infusion information 1114 at the plurality of sites in a start mode of operation. During the start mode, the control unit records the baseline data and generates a normal characterization of tissue. For example, an extravasation analysis may begin by determining a pre-injection baseline measurement of the tissue impedance by collecting preliminary data prior to injection.

In an illustrative example, monitoring beings by injecting a current across the monitored tissue 1116, measuring a parameter 1118 such as impedance during application of the current, and storing the parameter 1120 in a memory. In one example, a constant sinusoidal alternating current is applied to the first electrode pair at a current of approximately 200 uA and frequency of about 20 kHz and the voltage potential at the second electrode pair is measured. Other suitable currents and frequencies may be used. For example, Electrical Impedance Tomography imaging typically uses frequencies above 1 kHz and less than 100 kHz, although some applications may utilize frequencies up to 10 mHz and above. A system with capability to operate in a frequency range between 10 kHz and 10 MHz is highly flexible.

An increase or decrease in electrical conductance and capacitance may occur resulting from changes in the tissue.

Continuous calculations of tissue impedance are made during the injection therapy. The film barrier dressing remains affixed to the patient during monitoring. Monitoring continues over time 1121 and the measured and stored parameter is compared to past values 1122 including the stored baseline values. For multiple-site sensors, the infusion system compiles an impedance map 1124 that depicts impedance measurements over a two-dimensional or three-dimensional space.

A processor accesses the stored time and space impedance samples and performs a thresholding and pattern recognition operation 1126. The film barrier dressing remains affixed to the patient and monitoring continues over time during infusion. The infusion system determines the presence or absence of infiltration and extravasation 1128 based on the threshold analysis and pattern recognition operation, and conveys results to a display screen 1130 for visual notification of a caretaker.

In an example of a thresholding and pattern recognition operation 1126, if data such as photonics, optical, and impedance are acquired, the analysis may include operations of: (1) sensing infrared information and bio-impedance information, (2) comparing the information to preset thresholds, and (3) forming an information map indicative of the physical or geometric contours of the acquired parameter. Various types of information maps include photonics infrared reflection maps, optical spectrographics maps, and bio-impedance maps.

In one example, extravasation is indicated if the impedance changes with a substantially consistent slope of +0.5 Ω/s or more during infusion at a rate of at least 1000 cc over 24 hours or an intermittent infusion of over 100 cc in one hour.

In an example, tissue impedance is considered to be affected by extravasation because ionic contrast media has lower impedance than tissue. For ionic contrast media extravasation, measured impedance is less than the measured tissue impedance prior to extravasation. A non-ionic contrast media has higher impedance than tissue and causes increased impedance during an extravasation.

The infusion system can send an alert signal 1132, such as an audio annunciation or alarm, when a harmful condition occurs. Accordingly, the infusion system functions as a medical surveillance system to determine the condition of tissue as a patient receives an infusion to allow a caretaker to intervene early, reducing complications associated with intravascular infusion. The alert notification may also include transmission of the alert notification and analysis information in the form of a status report that are sent to a remote device, for example by wireless transmission of patient status information, for example to a computer, a pager, personal digital assistant (PDA), internet interface, or land line.

In another example, during the act of obtaining baseline pre-infusion information 1114, the baseline impedance represents the impedance measured at the zone of injection prior to starting injection. The pattern recognition operation 1126 determines the occurrence of extravasation by two characteristics, that the impedance varies from the baseline by more than a first predetermined threshold and that the rate of change of impedance, called the slope, is consistently larger than a second predetermined threshold.

To reduce false-positive indications of extravasation, a predetermined number of measurements are to deviate past the first predetermined threshold from the baseline, and the rate of change of the impedance measurements is to exceed a certain absolute value and do so consistently.

In another example, the thresholding and pattern recognition operation 1126 compiles individual historical and real time information on the status of a patient. Analyzed data includes continuously monitored data samples from one or more cross-sectional tissue areas. The time history of samples is analyzed to detect changes from reference information and baseline values, and monitor data trends. The analysis may include adjustments for known disease conditions, for example to predict likely trends and determine results outside the prediction. Rapid value changes may be indicative of physical movement or disruption of the needle or catheter at the insertion site.

The infusion system 100 can alternatively be used to monitor for physiological conditions relating to tissue grafting of artificial or natural tissue to detect the presence of tissue necrosis that may indicate rejection of new tissue.

In other applications the infusion system 100 can be used for monitoring, analysis, detection of complications, and generation of complication alarms in hydration monitoring, wound closure, pharmacokinetic monitoring, monitoring and mapping of tissue in multiple ablation freezing applications including radio frequency, laser, and cryosurgery applications, and others. For example, an infusion system 100 that monitors overhydration and hypersensitivity to infusions and infections may include temperature monitoring and heart electrical signal monitoring that can detect circulatory overload. Infections can cause elevation in temperature and circulatory overload causes the heart rate to increase.

In another example, conductivity maps may be used to determine a temperature distribution. Temperature mapping can be used for many applications including object recognition in noninvasive surgery while a surgeon cuts or ablates tissue by cryotherapy, knife, laser, radio frequency, or other cutting and ablating techniques. Mapping can be used to visualize cancer and reduce cutting of healthy tissue. Temperature mapping can be used for various applications including cancer treatment in liver and other organ tissues, breast biopsy, and the like. Temperature mapping using sensors in the frame of a dressing with an interior transparent window allows visualization in combination with temperature mapping. Temperature mapping can also be used in combination with ultrasound imaging.

Following generation of the alarm, a caretaker typically visually examines the site 1134 through the transparent dressing to detect IV complications such as dislodgement or movement of the catheter or needle from the original placement position. Complications are evidenced by visible blood, fluid beneath the dressing, or movement of the cannula or needle. Other visual cues of complication include tissue redness, swelling, tightness, and vein inflammation.

The caretaker can palpate the patient 1136 to detect tenderness or patient discomfort, swelling, or increase in skin temperature. Swelling may increase since IV infusions have an osmotic effect and draw water into the tissue.

The automatic alarm is a computer-aided diagnostic that enables the caretaker to assess patient condition to determine whether to continue or terminate the IV infusion. The automatic alarm gives a capacity for early detection of complications before symptoms are visible or before quickly arising complications reach critical levels. Upon detection of IV complications, the caretaker can terminate the infusion 1140.

Figure 12:
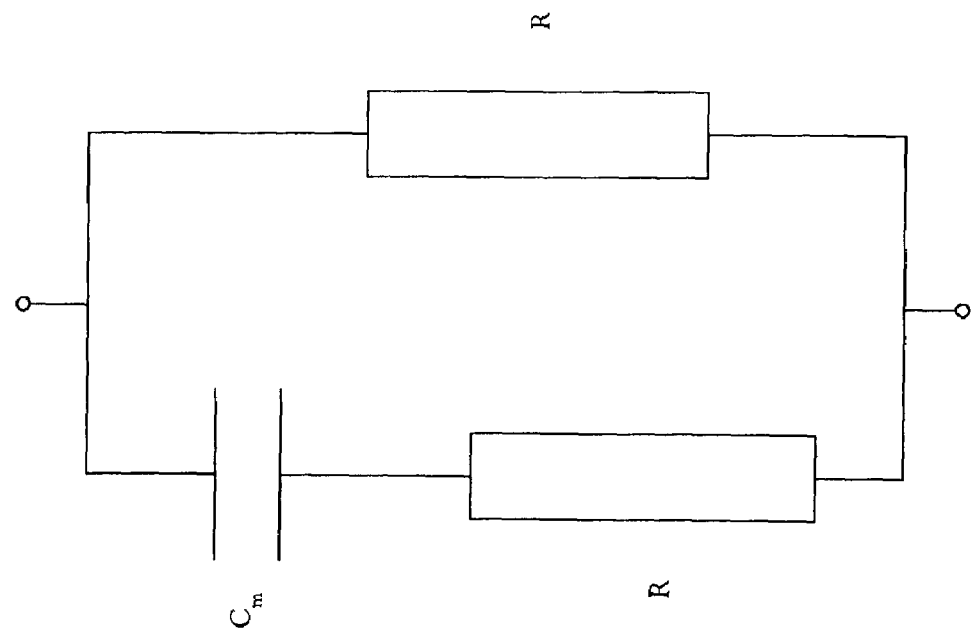
FIG. 12 is a schematic circuit diagram showing an impedance model of tissue that is useful for describing conductivity reconstruction in tissue.
Figure 12:
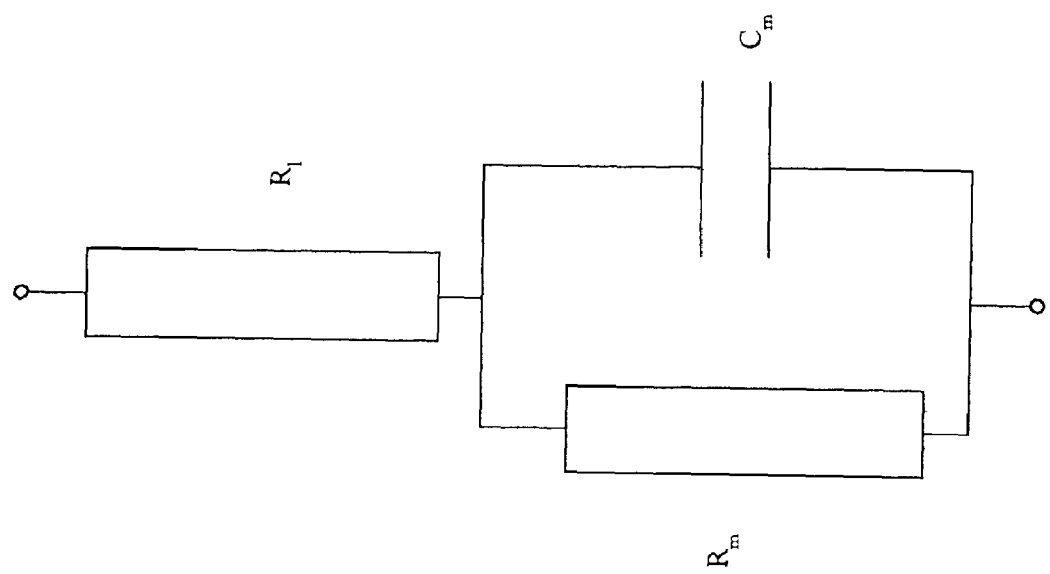

Referring to FIG. 12, a schematic circuit diagram shows an impedance model of tissue that is useful for describing conductivity reconstruction in tissue. Techniques for determining and mapping conductivity distribution in tissue supply useful information of anatomical and physiological status in various medical applications. Electrical Impedance Tomography (EIT) techniques are highly suitable for analyzing conductivity distribution. Electrical characteristics of tissue include resistive elements and capacitive elements. EIT techniques involve passing a low frequency current through the body to monitor various anatomical and physiological characteristics. The system can interrogate at multiple frequencies to map impedance. Analytical techniques involve forward and inverse solutions to boundary value analysis to tissue characteristics.

Multiple electrodes are placed in contact with tissue and a constant current is applied to the tissue across a subset of the electrodes, and impedance or resistance is measured at other electrodes. For example, tissue can be excited by an electric current and impedance is determined by measuring the electric potential generated by the current. In other examples, a voltage can be generated and a current measured. Current interrogation and voltage measurement typically produces a more accurate impedance measurement and has a lower output noise and better sensitivity. Conductivity distribution can be mapped in two dimensions or three dimensions. The illustrative technique solves the inverse problem in full three dimensions. Two dimensional images are obtained by slicing the three dimensional images.

Figure 13:
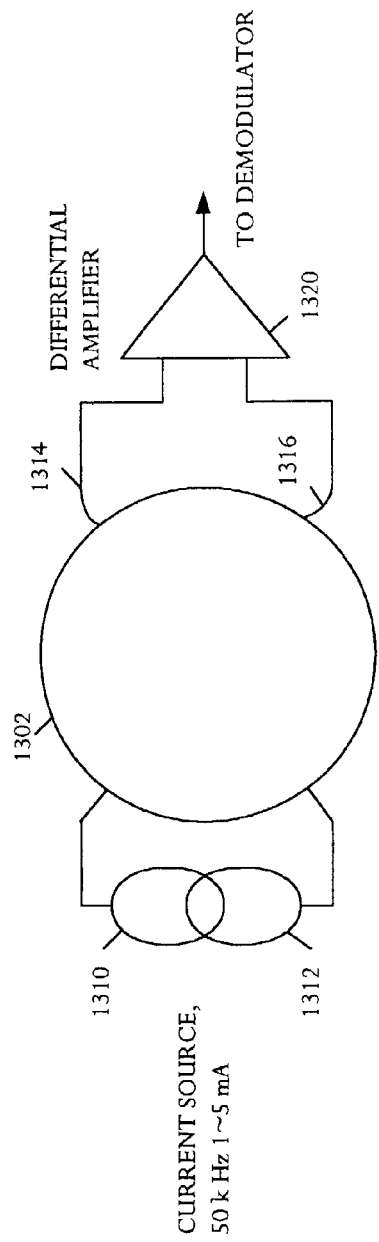
FIG. 13 is a schematic block diagram that illustrates an eight-electrode configuration for a tissue impedance measurement.

Referring to FIG. 13, a schematic block diagram shows an eight-electrode configuration for a tissue impedance measurement. The multiple electrodes can be connected to one impedance analysis circuit (not shown) via a multiplexer (not shown). Four electrodes 1310 are used to apply current to the tissue 1302, and four electrodes 1314 are used to sense body electrical activity that results from application of the current. The differential voltage evoked by the applied current is measured at a differential amplifier 1320. In an illustrative embodiment, the electrodes can be spaced equidistant about a circle, square, or any other suitable cross-section. The illustrative analysis technique is highly flexible allows three-dimensional imaging when the electrodes are formed in any configuration. In other embodiments, the electrodes need not be equidistant. Any number of electrodes may be used. For example, a suitable sensor can use 32 or any other number of electrodes. Generally, the electrodes are spaced with a sufficient gap for distinguishing electrical signals.

The illustrative imaging technique is very flexible and allows interrogation using any current pattern, using the complete electrodes model, rather than a point electrode model.

In one embodiment, the tomography method constructs a simple image with 15 pixels. Other image configurations are suitable.

Figure 14:
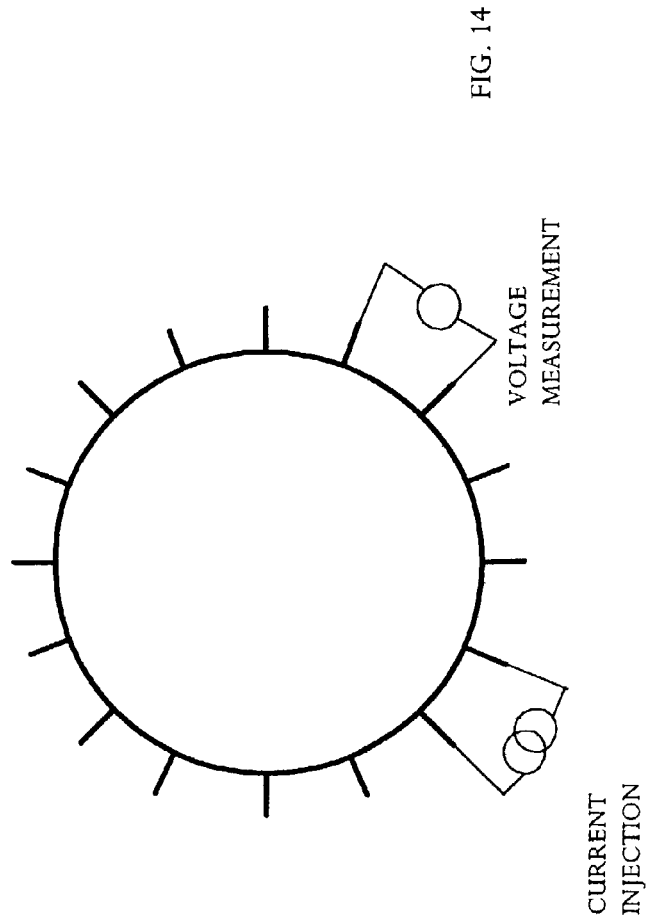
FIG. 14 is an Electrical Impedance Tomography (EIT) block diagram.

Referring to FIG. 14, an Electrical Impedance Tomography (EIT) block diagram shows a two-dimensional configuration of tissue at object B mapped by a conductivity measurement device. A mathematical model of the forward problem for conductivity is depicted in equations (3–6) as follows:

$$\nabla \cdot [\delta'(P) \cdot \nabla U'(P)] = 0 \text{ at object B} \quad (3)$$

$$\delta'(P)(\partial U'(P)/\partial \eta) = J \, P \in S \quad (4)$$

$$\int_S U'(P) ds = 0 \quad (5)$$

where U(P) is voltage and δ(P) is specific admittance of B, in which:

$$\delta'(P) = \delta(P) + j\omega \epsilon(P) \quad (6)$$

S is surface boundary of B.

A boundary value problem is defined in which conductivity distribution v is real and positive throughout the field, v is a potential distribution, η is an outward normal, J is applied flux, Ω is a domain of interest, and ∂Ω designates the domain boundary. The boundary value problem can be solved using a Finite Element Method (FEM) that produces a linear system of equations with the form shown in equation (7):

$$Yv = c \quad (7)$$

where Y is a global stiffness matrix, v is a vector representing the potential distribution at node of the elements and c is effective applied current at the nodes.

Figure 15:
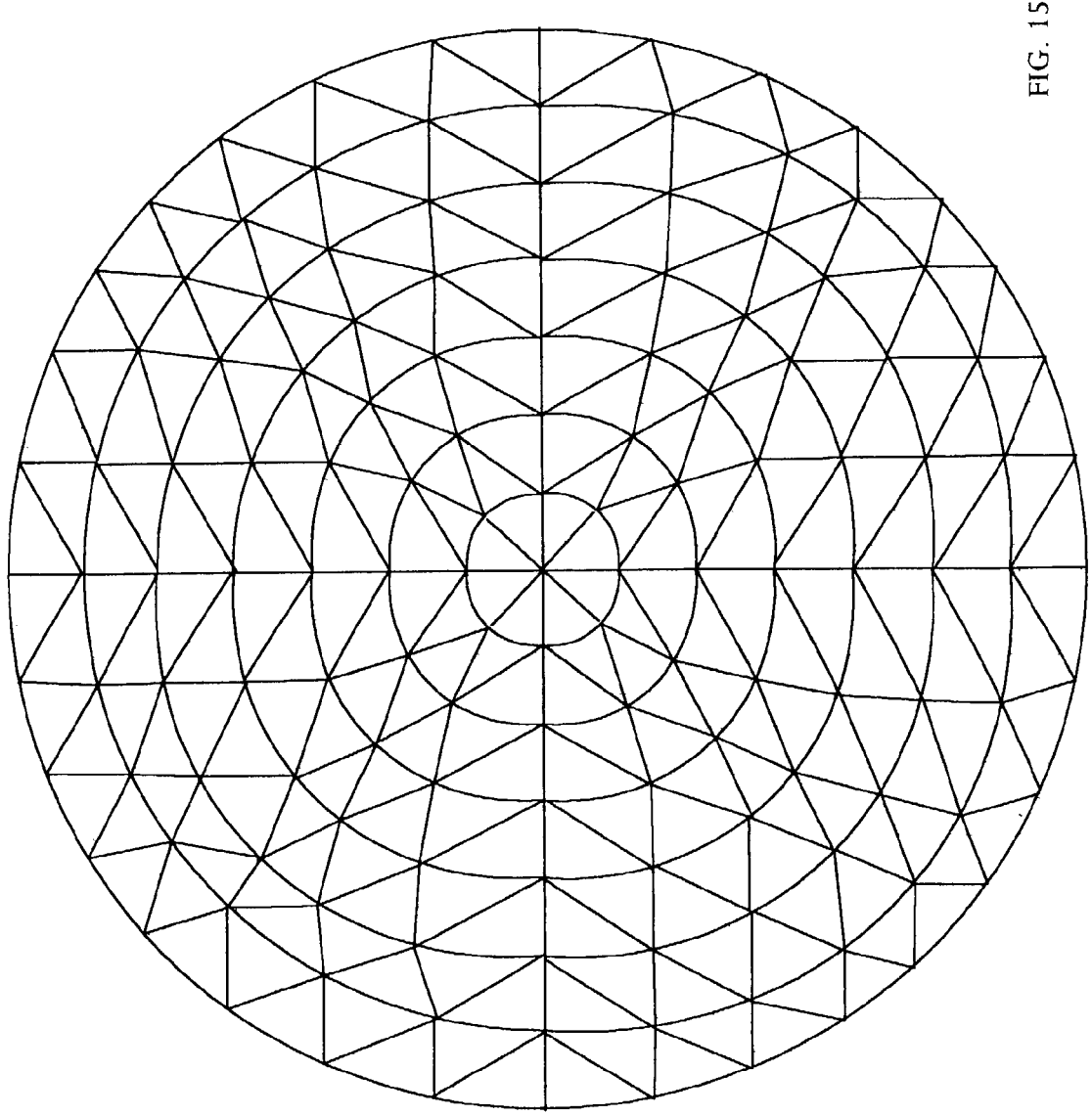
FIG. 15 is a schematic pictorial diagram showing a Finite Element Method (FEM) mesh.

Referring to FIG. 15, a schematic pictorial diagram shows a Finite Element Method (FEM) mesh. In the forward problem, the potential distribution of a domain is calculated given a known conductivity distribution and a known current source for boundary conditions. In the inverse problem analysis, a voltage is measured and the current injection pattern is known. From the known voltage and current injection pattern, the conductivity pattern is sought that produces the measured voltages. A difficulty is that in EIT, boundary potentials vary at any point in the conductivity distribution in a nonlinear manner.

The illustrative Electrical Impedance Tomography technique uses a regularized Newton-Raphson method to optimize the ill-posed inverse problem for imaging and mapping. The optimization problem attempts to find a best conductivity distribution that fits measured data. Image reconstruction uses nr to optimize the ill-posed inverse problem for imaging and mapping. The optimization problem attempts to find a best conductivity distribution that fits measured data. Image reconstruction uses Newton-Raphson regularization to stabilize the numerical solution of the ill-posed inverse problem. Image reconstruction based on the Newton-Raphson method uses an efficient method for Jacobian matrix computation. Tikhonov regularization is used in the Newton-Raphson method to stabilize image reconstruction.

The inverse problem in three dimensional Electrical Impedance Tomography imaging is ill-posed and nonlinear.

Several methods can be used for image reconstruction of both low and high contrast conductivity. EIT imaging can be cased on the Born approximation, particularly for low contrast conductivity reconstruction where little advantage is gained in recalculation of the Jacobian.

Figure 16:
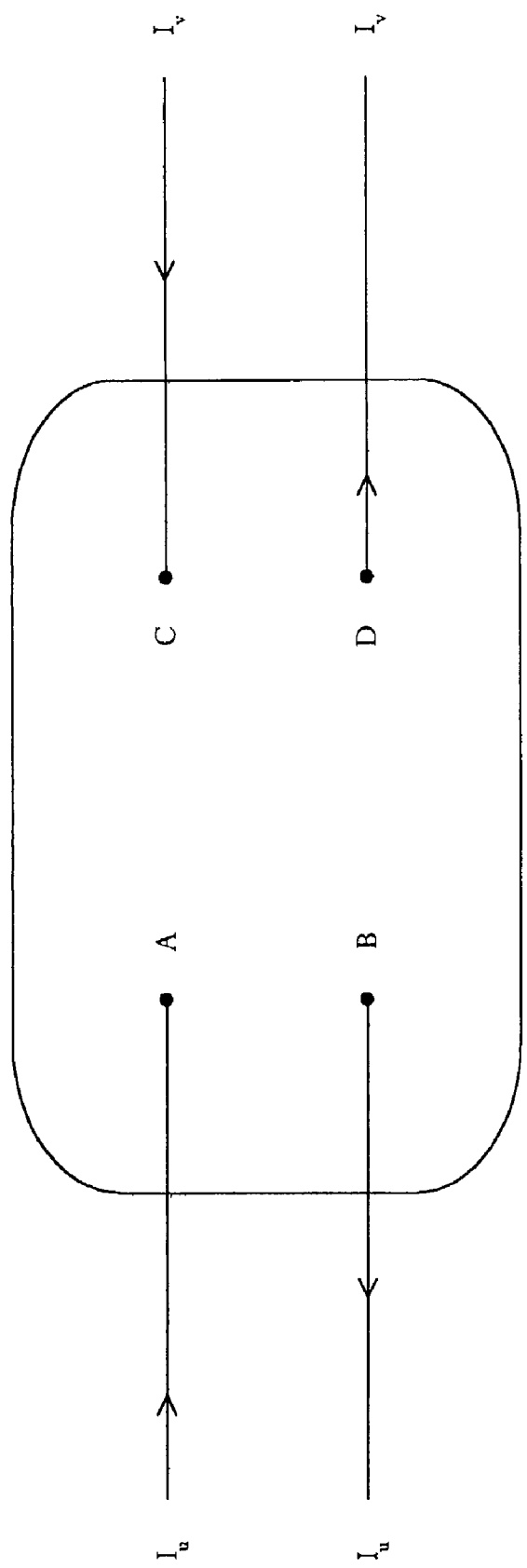
FIG. 16 is a highly schematic pictorial diagram that depicts sensitivity analysis using the Jacobian matrix.

Sensitivity Analysis using the Jacobian is depicted according to FIG. 16. When a conductivity distribution changes from σ to σ+Δσ, the transfer impedance change ΔZ for pairs of current and voltage electrodes A,B and C,D, respectively are shown in equation (8):

$$\Delta Z = -\int_\Omega \Delta \sigma (\nabla u(\sigma)/I_u) \cdot (\nabla v(\sigma + \Delta \sigma)/I_v) d\Omega \quad (8)$$

where u is the potential distribution over the field when the current $I_u$ is applied at electrodes A,B with a conductivity of σ. Similarly, v is potential over the field when the current $I_v$ is applied at electrodes C,D with a conductivity of σ+Δσ. Equation (8) assists solution of the inverse problem by allowing estimation of a conductivity σ and calculation of u given current $I_u$ in the forward analysis. The difference between the calculated potential distribution u and the measured potential distribution v gives value ΔZ. Using value ΔZ, conductivity distribution Δσ can be solved. The sensitivity method is very general and allows determination of sensitivity directly and with any distribution of conductivity. Other less suitable methods only allow calculation of sensitivity in a homogenous conductivity area.

A Newton-Raphson technique can be used to minimize a function φ with respect to σ defined according to equation (9):

$$\phi = \tfrac{1}{2}(f-V)^T(f-V) \quad (9)$$

Minimization of φ is the Gauss-Newton iteration shown in equation (10):

$$\Delta \sigma_k = -[f'(\sigma_k)^T f'(\sigma_k)]^{-1} f'(\sigma_k)^T [f(\sigma_k) - V] \quad (10)$$

The φ iteration is ill-conditioned and further exacerbated by noisy data.

A simple iterative scheme can be used to combine the forward problem and the inverse problem. First, estimate $\sigma_k$ and consequently calculated Second, compare the calculated f and the measured V. Third, adjust $\sigma_k$ and calculate a new f Fourth, iterate until ‖V−f‖ reaches a specified criterion.

Figure 17:
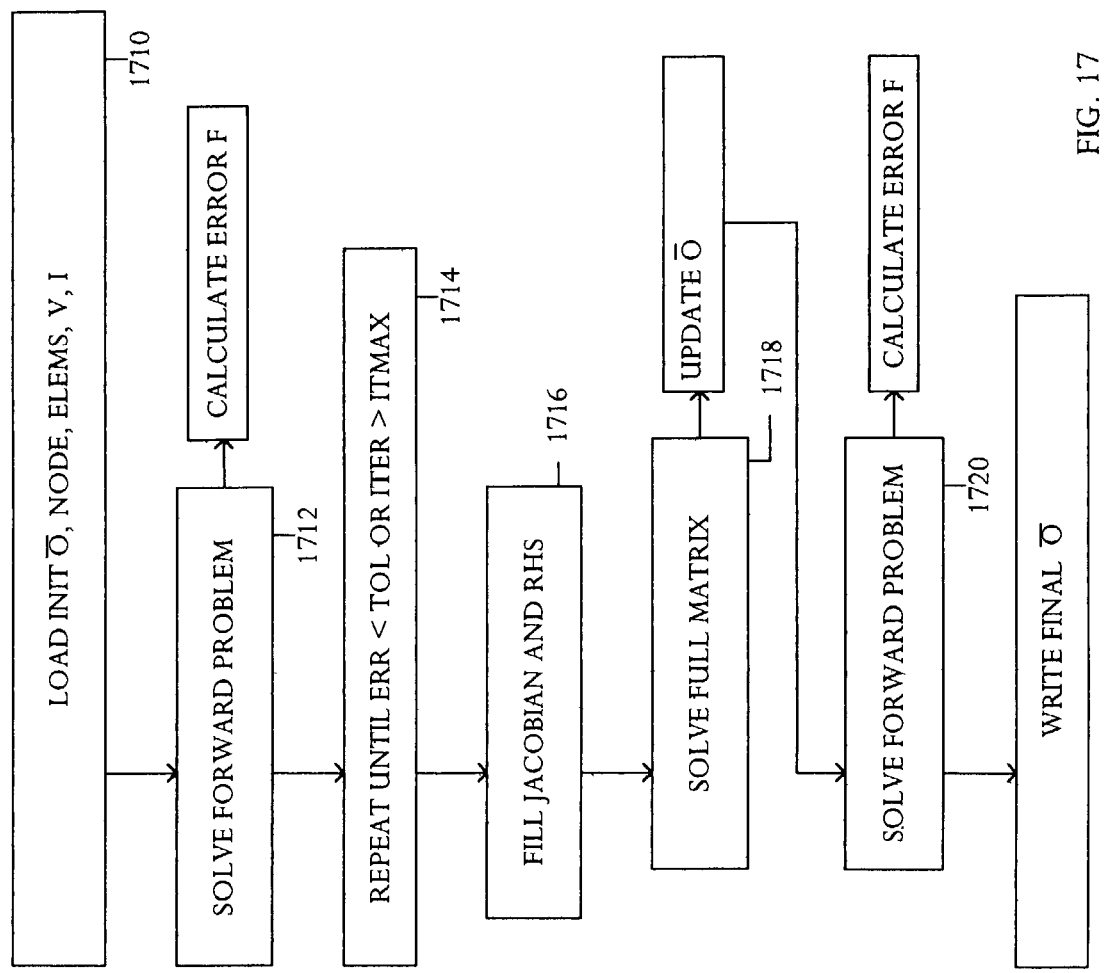
FIG. 17 is a flow chart that illustrates an embodiment of a reconstruction method for Electrical Impedance Tomography.

In a regularized Newton-Raphson method depicted in FIG. 17, an initial conductivity distribution is given 1710 which is presumed to be zero. The forward problem is solved 1712 and predicted voltages are compared with calculated voltages from the finite element model. Conductivity is updated using a regularized inverse of the Jacobian. The process is repeated 1714 until predicted voltages from the finite element method agree with measured voltages. The update formula is shown in equation (11):

$$\sigma_{n+1} = \sigma_n + (J_n^* J_n + R)^{-1} J_n^* (V_{measured} - F(\sigma_n)) \quad (11)$$

$J_n$ is the Jacobian calculated 1716 with the conductivity $\sigma_n$. $V_{measured}$ is the vector of voltage measurements and the forward solution $F(\sigma_n)$ is the predicted voltage from the finite element model with conductivity $\sigma_n$. The matrix R is a regularization matrix that penalized extreme changes in conductivity, correcting instability in the reconstruction at the expense of producing artificially smooth images. To solve the full matrix inverse problem 1718, information obtained from the forward measurement is used. The inverse problem calculates a conductivity distribution $\sigma_n$ given a set of current injection patterns I and a set of measured voltages V. The forward problem 1720 calculates voltages f given a current injection pattern I and a conductivity distribution σ 1722.

While the invention has been described with reference to various embodiments, it will be understood that these embodiments are illustrative and that the scope of the invention is not limited to them. Many variations, modifications, additions and improvements of the embodiments described are possible. For example, those skilled in the art will readily implement the steps necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims.

In the claims, unless otherwise indicated the article "a" is to refer to "one or more than one."

What is claimed is:

1. An imaging apparatus comprising:
   a control unit capable of coupling to a plurality of electrodes, the control unit capable of controlling the electrodes to sense one or more parameters indicative of tissue condition;
   an interrogating process executable on the control unit that generates an interrogation signal for application to the electrodes;
   a measuring process executable on the control unit that measures a response evoked by the interrogation signal;
   a potentiometric sensor capable of testing electrolytes and selected ions by measuring a voltage gradient across a metabolic sample; and
   a pattern recognition process executable on the control unit that analyzes the response evoked by the interrogation signal and that analyzes tissue based on the voltage gradients, and executes forward and inverse solutions to a boundary value analysis to determine tissue characteristics.

2. An imaging apparatus according to claim 1 wherein:
   the interrogation signal is a current passed through one or more electrodes end the measuring process measures a voltage signal at one or more electrodes to determine impedance.

3. An imaging apparatus according to claim 1 wherein:
   the interrogation signal is a voltage applied to one or more of the electrodes and the measuring process measures a current signal at one or more electrodes to determine impedance.

4. An imaging apparatus according to claim 1 wherein:
   the pattern recognition process calculates a potential distribution of a domain given a known conductivity distribution and a known current source for the boundary conditions in a forward problem and measures a voltage for a known current injection pattern in an inverse problem.

5. An imaging apparatus according to claim 1 wherein:
   the pattern recognition process uses a regularized Newton-Raphson method to optimize an ill-posed inverse problem for imaging and tissue mapping.

6. An imaging apparatus according to claim 1 further comprising:
   an iterative process that combines a forward problem and an inverse problem, iterations including:
   estimating conductance and calculating voltage,
   comparing the calculated voltage with a measured voltage,
   adjusting conductivity and calculating a new estimated voltage, and
   iterating until the calculated and measured voltages are within a specified criteria.

7. An imaging apparatus according to claim 1 wherein:
   the pattern recognition process calculates a predicted voltage based on a finite element model using a known conductivity.

8. An imaging apparatus according to claim 1 further comprising:
   means for determining an initial conductivity distribution;
   means for solving a forward boundary value problem to determine a predicted voltage using a finite element model;
   means for comparing the predicted voltage with voltages calculated from the finite element model;
   means for repeating the forward boundary value problem and the comparison of predicted and calculated voltages until a predetermined criteria is met;
   means for calculating the Jacobian; and
   means for solving a full matrix inverse boundary value problem using information obtained from the forward problem.

9. An imaging apparatus according to claim 8 wherein: the initial conductivity distribution is presumed to be zero.

10. An imaging apparatus according to claim 8 further comprising:
    means for updating the conductivity using a regularized inverse of the Jacobian.

11. An imaging apparatus according to claim 8 further comprising:
    means for calculating the Jacobian using a regularization matrix that penalized extreme changes in conductivity and corrects instability in reconstruction at a cost of producing artificially smooth images.

12. An imaging apparatus according to claim 8 wherein:
    the inverse boundary value problem calculates a conductivity distribution given a current set of current injection patterns and a set of measured voltages.

13. An imaging apparatus according to claim 8 wherein:
    the forward boundary value problem calculates voltages given a known current injection pattern and a measured conductivity distribution.

14. An imaging apparatus according to claim 1 wherein:
    the imaging apparatus executes a multiple-frequency analysis.

15. An imaging method comprising:
    testing electrolytes and selected ions by measuring a voltage gradient across a metabolic sample;
    determining an initial conductivity distribution;
    solving a forward boundary value problem to determine a predicted voltage using a finite element model;
    comparing the predicted voltage with voltages calculated from the finite element model;
    repeating the forward boundary value problem and the comparison of predicted and calculated voltages until a predetermined criteria is met;
    calculating the Jacobian;
    solving a full matrix inverse boundary value problem using information obtained from the forward problem; and
    analyzing tissue based on the voltage gradients and a solution to the full matrix inverse boundary value problem.

16. An imaging method according to claim 15 further comprising:

calculating the Jacobian using a regularization matrix that penalized extreme changes in conductivity and corrects instability in reconstruction at a cost of producing artificially smooth images.

17. An imaging method according to claim 15 further comprising:
executing a multiple-frequency analysis.

18. An imaging apparatus comprising:
a control unit capable of coupling to one or more sensors, the control unit capable of controlling the sensors to sense one or more parameters indicative of tissue condition;
a measuring process executable on the control unit that measures a signal indicative of tissue condition from the one or more sensors;
a potentiometric sensor capable of testing electrolytes and selected ions by measuring a voltage gradient across a metabolic sample; and
a pattern recognition process executable on the control unit that analyzes the measured signal and analyzes tissue based on the voltage gradients, and executes forward and inverse solutions to a boundary value analysis to determine tissue characteristics.

19. An imaging apparatus according to claim 18 further comprising:
a thermography sensor wherein the pattern recognition process forms an image based on tissue temperature signals.

* * * * *